(12) United States Patent
Nishimura et al.

(10) Patent No.: US 7,129,063 B2
(45) Date of Patent: Oct. 31, 2006

(54) EXOCRINE GLAND TIGHT JUNCTION-CONSTITUTING PROTEIN JEAP FAMILY

(75) Inventors: Miyuki Nishimura, Kyoto (JP); Mayumi Asano, Ogaki (JP); Yuichi Ono, Ibaraki (JP); Koji Morimoto, Neyagawa (JP); Masakazu Takeuchi, Kyoto (JP); Yoko Inoue, Kyoto (JP); Toshio Imai, Kyoto (JP); Yoshimi Takai, Kobe (JP)

(73) Assignee: Eisai Co., Ltd., Tokyo (JP)

( * ) Notice: Subject to any disclaimer, the term of this patent is extended or adjusted under 35 U.S.C. 154(b) by 111 days.

(21) Appl. No.: 10/298,417

(22) Filed: Nov. 15, 2002

(65) Prior Publication Data
US 2003/0124603 A1    Jul. 3, 2003

(30) Foreign Application Priority Data
Nov. 16, 2001  (JP)  ............... 2001-352241

(51) Int. Cl.
C12P 21/02 (2006.01)
C12N 15/63 (2006.01)
C12N 1/21 (2006.01)
C12N 1/19 (2006.01)
C12N 5/10 (2006.01)
C07H 21/04 (2006.01)

(52) U.S. Cl. ............... 435/69.1; 435/320.1; 435/252.3; 435/254.11; 435/325; 536/23.5

(58) Field of Classification Search ............... 435/69.1; 526/23.1; 530/350
See application file for complete search history.

(56) References Cited
U.S. PATENT DOCUMENTS
6,783,969 B1 * 8/2004 Tang et al. ............... 435/219

FOREIGN PATENT DOCUMENTS
WO    WO 99/66038    12/1999

OTHER PUBLICATIONS

Kessler et al. Database Genbank Accession No. AF175968. National Library of Medicine, Bethesda, MD (Aug. 6, 1999).*
Adachi, et al. "*Mus musculus* adult make testis cDNA, Riken full-length enriched library, clone:4932416D09 product:B-Motin (Fragment) homolog [*Homo sapiens*], full insert sequence." Database accession No. ak016526, XP002237595 (Feb. 9, 2001).
Kessler, et al. "*Mus musculus* angiomotin-like protein 2 variant 1 (Amot 12) mRNA, partial cds." Database accession No. AF175967, XP002237586 (Sep. 26, 1999).
Ohara, et al. "*Homo sapiens* Amotl2 mRNA for angiomotin like 2, partial cds, other name:KIAA0989." Database accession No. AB0232C6, XP002237597 (Apr. 9, 1999).
Strausberg. "*Mus musculus*, Similar to angiomotin like 2, clone MGC:36419 IMAGE:5323888,DE mRNA, complete cds." Database accession No. BC027824, XP0022387598 (May 3, 2002).
Nishimura, et al. JEAP, A Novel Component of Tight Junctions in Exocrine Cells, *The Journal of Biological Chemistry*, vol. 277, No. 7, pp. 5583-5587, 2002.

* cited by examiner

*Primary Examiner*—Robert A. Wax
(74) *Attorney, Agent, or Firm*—Choate, Hall & Stewart, LLP

(57) ABSTRACT

A mouse cDNA library from gene fragments encoding proteins localizing at cell-cell junctions was screened by a technique visualizing localization of a protein to to identify a junction-enriched and -associated protein, JEAP. GenBank homology search was performed based on the sequence. Based on the obtained sequence, a mouse cDNA library was screened to identify JEAP-2. By using prepared antibodies against these proteins, it was revealed that these proteins express specifically at tight junctions, in particular, tight junctions in exocrine glands.

8 Claims, 6 Drawing Sheets

JEAP

JEAP-2

SEQUENCE LISTING

<160> NUMBER OF SEQ ID NOS: 10

<210> SEQ ID NO 1
<211> LENGTH: 2649
<212> TYPE: DNA
<213> ORGANISM: Mus musculus
<220> FEATURE:
<221> NAME/KEY: CDS
<222> LOCATION: (1)..(2649)

<400> SEQUENCE: 1

```
atg aga ggt tct gag gat gta gcc tct gga aga gtg tta cag cgg ctg      48
Met Arg Gly Ser Glu Asp Val Ala Ser Gly Arg Val Leu Gln Arg Leu
 1               5                  10                  15 atc cag gaa caa ctg cgc tat ggc acc cca act gag aac atg aac ctg      96
Ile Gln Glu Gln Leu Arg Tyr Gly Thr Pro Thr Glu Asn Met Asn Leu
             20                  25                  30 ctg gcc att cag cac cag gcc aca ggg agt gca ggg cca gcc cac gcc     144
Leu Ala Ile Gln His Gln Ala Thr Gly Ser Ala Gly Pro Ala His Ala
         35                  40                  45 acc acc aac ttt tct tcc acg gaa acc ctc act caa gaa gat cca caa     192
Thr Thr Asn Phe Ser Ser Thr Glu Thr Leu Thr Gln Glu Asp Pro Gln
     50                  55                  60 atg gtc tat cag tcg gcc cgc caa gaa ccg cag ggt caa gag cat cag     240
Met Val Tyr Gln Ser Ala Arg Gln Glu Pro Gln Gly Gln Glu His Gln
 65                  70                  75                  80 gga gac aat acg gtg atg gag aag cag gtc cgg tcc aca cag cct cag     288
Gly Asp Asn Thr Val Met Glu Lys Gln Val Arg Ser Thr Gln Pro Gln
                 85                  90                  95 cag aac aac gag gag ctc ccc acg tat gag gaa gcc aag gcc cag tcc     336
Gln Asn Asn Glu Glu Leu Pro Thr Tyr Glu Glu Ala Lys Ala Gln Ser
            100                 105                 110 cag ttc ttc agg gga cag cag cag cag cag caa cag cag cag cag caa     384
Gln Phe Phe Arg Gly Gln Gln Gln Gln Gln Gln Gln Gln Gln Gln Gln
        115                 120                 125 cag cag cag caa cag cag cag gga cag ggg ccc ctt agc cac act tat     432
Gln Gln Gln Gln Gln Gln Gln Gly Gln Gly Pro Leu Ser His Thr Tyr
    130                 135                 140 tac atg gcc gga ggt acc agt cag aag tcc cgc act gag ggg agg ccc     480
Tyr Met Ala Gly Gly Thr Ser Gln Lys Ser Arg Thr Glu Gly Arg Pro
145                 150                 155                 160 aca gtg aac cgg gcc aac agt gga cag gcg cat aag gat gag gcc ctg     528
Thr Val Asn Arg Ala Asn Ser Gly Gln Ala His Lys Asp Glu Ala Leu
                165                 170                 175 aaa gaa cta aag cag ggc cat gtc cgg tcc ctc agt gag agg atc atg     576
Lys Glu Leu Lys Gln Gly His Val Arg Ser Leu Ser Glu Arg Ile Met
            180                 185                 190 cag ctg tca ctg gag agg aat ggg gct aag caa cac ctc ccc agc tct     624
Gln Leu Ser Leu Glu Arg Asn Gly Ala Lys Gln His Leu Pro Ser Ser
        195                 200                 205 gga aat gga aag agc ttc aaa gct gga gga gag cca tcc cca gct cag     672
```

```
                Gly Asn Gly Lys Ser Phe Lys Ala Gly Gly Glu Pro Ser Pro Ala Gln
                    210                 215                 220 cct gtc tgt aaa gca ctg gac cct cgt ggc cct cca cct gaa tac ccc          720
Pro Val Cys Lys Ala Leu Asp Pro Arg Gly Pro Pro Glu Tyr Pro
225                 230                 235                 240 ttc aag acc aag cca atg aaa tcc cca gtc agc aag aac caa gat cac          768
Phe Lys Thr Lys Pro Met Lys Ser Pro Val Ser Lys Asn Gln Asp His
                245                 250                 255 ggt ctt tac tac aat gac cag cac cct ggg gta ctc cat gag atg gtc          816
Gly Leu Tyr Tyr Asn Asp Gln His Pro Gly Val Leu His Glu Met Val
            260                 265                 270 aaa cct tac cca gca cct cag cct gcg aga aca gaa gtg gcc gtc ctg          864
Lys Pro Tyr Pro Ala Pro Gln Pro Ala Arg Thr Glu Val Ala Val Leu
        275                 280                 285 agg tat cag cca ccc ccg gag tat ggc gtc acc agc cgg ccc tgc cag          912
Arg Tyr Gln Pro Pro Pro Glu Tyr Gly Val Thr Ser Arg Pro Cys Gln
    290                 295                 300 ctg cct ttt cca tct acg gtg cag cag cat agc ccc atg tcc tct cag          960
Leu Pro Phe Pro Ser Thr Val Gln Gln His Ser Pro Met Ser Ser Gln
305                 310                 315                 320 acc tcc tcc atc ggt ggt act ctg cac tcc gtc tcc ctg cct ctt cca         1008
Thr Ser Ser Ile Gly Gly Thr Leu His Ser Val Ser Leu Pro Leu Pro
                325                 330                 335 ctt ccc ata agc ctg gcg gct tca cag ccc cta cca gcc tcc ccc aac         1056
Leu Pro Ile Ser Leu Ala Ala Ser Gln Pro Leu Pro Ala Ser Pro Asn
            340                 345                 350 cag cag ctt gga ccg gat gcc ttt gcg att gtg gag cga gcc cag caa         1104
Gln Gln Leu Gly Pro Asp Ala Phe Ala Ile Val Glu Arg Ala Gln Gln
        355                 360                 365 atg gta gag atc ctg aca gag gag aac cgt gtg ctt cac cag gag ctt         1152
Met Val Glu Ile Leu Thr Glu Glu Asn Arg Val Leu His Gln Glu Leu
    370                 375                 380 cag ggc tgc tat gac aac gct gac aag ctc cac aag ttt gaa aaa gag         1200
Gln Gly Cys Tyr Asp Asn Ala Asp Lys Leu His Lys Phe Glu Lys Glu
385                 390                 395                 400 ctg cag agt att tcg gag gcc tac gag agc ctg gtc aag tcc acc acc         1248
Leu Gln Ser Ile Ser Glu Ala Tyr Glu Ser Leu Val Lys Ser Thr Thr
                405                 410                 415 aag cgt gag tct ctg gac aag gca atg aga acc aag ctc gaa ggc gag         1296
Lys Arg Glu Ser Leu Asp Lys Ala Met Arg Thr Lys Leu Glu Gly Glu
            420                 425                 430 ata agg aga ctt cat gac ttc aac aga gat ctc cga gat cga ctg gag         1344
Ile Arg Arg Leu His Asp Phe Asn Arg Asp Leu Arg Asp Arg Leu Glu
        435                 440                 445 aca gcc aac agg cag ctg tcc agc agg gaa tac gat ggg cat gaa gac         1392
Thr Ala Asn Arg Gln Leu Ser Ser Arg Glu Tyr Asp Gly His Glu Asp
    450                 455                 460 aaa gct gca gag agc cat tac gtg tcc cag aac aaa gaa ttc ttg aag         1440
Lys Ala Ala Glu Ser His Tyr Val Ser Gln Asn Lys Glu Phe Leu Lys
465                 470                 475                 480 gaa aag gaa aag ttg gaa atg gag ttg gca gca gtg cgt acg gca agt         1488
Glu Lys Glu Lys Leu Glu Met Glu Leu Ala Ala Val Arg Thr Ala Ser
                485                 490                 495 gag gac cat cgg agg cac atc gag atc ctg gac cag gct ttg agc aat         1536
Glu Asp His Arg Arg His Ile Glu Ile Leu Asp Gln Ala Leu Ser Asn
            500                 505                 510 gcg cag gct aga gtg atc aaa ctg gag gaa gag tta cga gag aag caa         1584
Ala Gln Ala Arg Val Ile Lys Leu Glu Glu Glu Leu Arg Glu Lys Gln
        515                 520                 525
```

```
gcc tat gtg gaa aag gtg gag aag ctg cag cag gcc ctg acc cag ctg    1632
Ala Tyr Val Glu Lys Val Glu Lys Leu Gln Gln Ala Leu Thr Gln Leu
530             535                 540 cag tca gcg tgc gag aag cga ggg cag atg gaa cgc agg ttg cgg acc    1680
Gln Ser Ala Cys Glu Lys Arg Gly Gln Met Glu Arg Arg Leu Arg Thr
545                 550                 555                 560 tgg ctg gag agg gag cta gac gct ctg agg aca cag cag aaa cat ggc    1728
Trp Leu Glu Arg Glu Leu Asp Ala Leu Arg Thr Gln Gln Lys His Gly
                565                 570                 575 aca ggc cct cca gtc agt ctc cca gaa tgt aat gct cct gcc ctc atg    1776
Thr Gly Pro Pro Val Ser Leu Pro Glu Cys Asn Ala Pro Ala Leu Met
            580                 585                 590 gag ctg gtg agg gag aag gag gag cgg atc ctc gcc ttg gag gcc gac    1824
Glu Leu Val Arg Glu Lys Glu Glu Arg Ile Leu Ala Leu Glu Ala Asp
        595                 600                 605 atg acc aag tgg gag cag aag tac ctg gaa gag agc acc atc cgg cac    1872
Met Thr Lys Trp Glu Gln Lys Tyr Leu Glu Glu Ser Thr Ile Arg His
610                 615                 620 ttt gcc atg agc gca gct gcc gct gcc aca gcc gag agg gac acc acc    1920
Phe Ala Met Ser Ala Ala Ala Ala Ala Thr Ala Glu Arg Asp Thr Thr
625                 630                 635                 640 atc agc aac cac tcg agg aat ggc agc tat ggg gag agc tcc ctg gag    1968
Ile Ser Asn His Ser Arg Asn Gly Ser Tyr Gly Glu Ser Ser Leu Glu
                645                 650                 655 gcc cac atc tgg cca gag gaa gaa gaa gtg gtg cag gcc aac agg agg    2016
Ala His Ile Trp Pro Glu Glu Glu Glu Val Val Gln Ala Asn Arg Arg
            660                 665                 670 tgt cag gac atg gag tac act att aaa aac ctc cat gcc aaa atc ata    2064
Cys Gln Asp Met Glu Tyr Thr Ile Lys Asn Leu His Ala Lys Ile Ile
        675                 680                 685 gag aag gat gcc atg ata aag gtc ctg cag cag cga tcc cgt aag gat    2112
Glu Lys Asp Ala Met Ile Lys Val Leu Gln Gln Arg Ser Arg Lys Asp
690                 695                 700 gct ggg aag acg gac tct gcc agc ctg agg cct gcc cgc tct gtc cca    2160
Ala Gly Lys Thr Asp Ser Ala Ser Leu Arg Pro Ala Arg Ser Val Pro
705                 710                 715                 720 tcc atc gct gcg gcc act ggg aca cat tct cgc cag act tct ctt acc    2208
Ser Ile Ala Ala Ala Thr Gly Thr His Ser Arg Gln Thr Ser Leu Thr
                725                 730                 735 agc agc cag ctg aca gaa gag aaa aag gaa gag aag acg acc tgg aaa    2256
Ser Ser Gln Leu Thr Glu Glu Lys Lys Glu Glu Lys Thr Thr Trp Lys
            740                 745                 750 ggg agt ata gga ttc ctg ctg gga aag gaa cac cag gga cag gca tct    2304
Gly Ser Ile Gly Phe Leu Leu Gly Lys Glu His Gln Gly Gln Ala Ser
        755                 760                 765 gcc cct ctg ctg ccg acc aca cct gcc tct gca ttg tcc ctt ccg gcc    2352
Ala Pro Leu Leu Pro Thr Thr Pro Ala Ser Ala Leu Ser Leu Pro Ala
770                 775                 780 tct acc aca tcg gcc agc agc acc cac gcc aag acg ggc agc aag gac    2400
Ser Thr Thr Ser Ala Ser Ser Thr His Ala Lys Thr Gly Ser Lys Asp
785                 790                 795                 800 agc agc aca cag acc gac aag agc acg gag ctc ttc tgg ccc agc atg    2448
Ser Ser Thr Gln Thr Asp Lys Ser Thr Glu Leu Phe Trp Pro Ser Met
                805                 810                 815 gct tcc ctc ccc agc cgt ggc agg ctg agc aca gcc cct tcc aac agc    2496
Ala Ser Leu Pro Ser Arg Gly Arg Leu Ser Thr Ala Pro Ser Asn Ser
            820                 825                 830 ccc atc cta aag cat cca gct gcc aaa gga gcc gtg gag aag cag gag    2544
Pro Ile Leu Lys His Pro Ala Ala Lys Gly Ala Val Glu Lys Gln Glu
        835                 840                 845
```

-continued

| | | | | | | | | | | | | |
|---|---|---|---|---|---|---|---|---|---|---|---|---|
| aac | tct | cct | ggt | cat | ggg | aag | gca | tcg | gag | cac | aga | ggc | cga | gtc | agc | 2592 |
| Asn | Ser | Pro | Gly | His | Gly | Lys | Ala | Ser | Glu | His | Arg | Gly | Arg | Val | Ser | |
| 850 | | | | | 855 | | | | | 860 | | | | | | |

| aac | ttg | ctg | cac | aag | cct | gag | ttc | cca | gat | ggc | gag | atg | atg | gaa | gtg | 2640 |
| Asn | Leu | Leu | His | Lys | Pro | Glu | Phe | Pro | Asp | Gly | Glu | Met | Met | Glu | Val | |
| 865 | | | | 870 | | | | | 875 | | | | | 880 | | |

| ctc | atc | tag | | | | | | | | | | | | | | 2649 |
| Leu | Ile | | | | | | | | | | | | | | | |

<210> SEQ ID NO 2
<211> LENGTH: 882
<212> TYPE: PRT
<213> ORGANISM: Mus musculus

<400> SEQUENCE: 2

Met Arg Gly Ser Glu Asp Val Ala Ser Gly Arg Val Leu Gln Arg Leu
 1               5                  10                  15

Ile Gln Glu Gln Leu Arg Tyr Gly Thr Pro Thr Glu Asn Met Asn Leu
             20                  25                  30

Leu Ala Ile Gln His Gln Ala Thr Gly Ser Ala Gly Pro Ala His Ala
         35                  40                  45

Thr Thr Asn Phe Ser Ser Thr Glu Thr Leu Thr Gln Glu Asp Pro Gln
     50                  55                  60

Met Val Tyr Gln Ser Ala Arg Gln Glu Pro Gln Gly Gln Glu His Gln
 65                  70                  75                  80

Gly Asp Asn Thr Val Met Glu Lys Gln Val Arg Ser Thr Gln Pro Gln
                 85                  90                  95

Gln Asn Asn Glu Glu Leu Pro Thr Tyr Glu Glu Ala Lys Ala Gln Ser
            100                 105                 110

Gln Phe Phe Arg Gly Gln Gln Gln Gln Gln Gln Gln Gln Gln Gln Gln
        115                 120                 125

Gln Gln Gln Gln Gln Gln Gly Gln Gly Pro Leu Ser His Thr Tyr
    130                 135                 140

Tyr Met Ala Gly Gly Thr Ser Gln Lys Ser Arg Thr Glu Gly Arg Pro
145                 150                 155                 160

Thr Val Asn Arg Ala Asn Ser Gly Gln Ala His Lys Asp Glu Ala Leu
                165                 170                 175

Lys Glu Leu Lys Gln Gly His Val Arg Ser Leu Ser Glu Arg Ile Met
            180                 185                 190

Gln Leu Ser Leu Glu Arg Asn Gly Ala Lys Gln His Leu Pro Ser Ser
        195                 200                 205

Gly Asn Gly Lys Ser Phe Lys Ala Gly Gly Glu Pro Ser Pro Ala Gln
    210                 215                 220

Pro Val Cys Lys Ala Leu Asp Pro Arg Gly Pro Pro Glu Tyr Pro
225                 230                 235                 240

Phe Lys Thr Lys Pro Met Lys Ser Pro Val Ser Lys Asn Gln Asp His
                245                 250                 255

Gly Leu Tyr Tyr Asn Asp Gln His Pro Gly Val Leu His Glu Met Val
            260                 265                 270

Lys Pro Tyr Pro Ala Pro Gln Pro Ala Arg Thr Glu Val Ala Val Leu
        275                 280                 285

Arg Tyr Gln Pro Pro Glu Tyr Gly Val Thr Ser Arg Pro Cys Gln
    290                 295                 300

Leu Pro Phe Pro Ser Thr Val Gln Gln His Ser Pro Met Ser Ser Gln
305                 310                 315                 320

-continued

```
Thr Ser Ser Ile Gly Gly Thr Leu His Ser Val Ser Leu Pro Leu Pro
                325                 330                 335

Leu Pro Ile Ser Leu Ala Ala Ser Gln Pro Leu Pro Ala Ser Pro Asn
                340                 345                 350

Gln Gln Leu Gly Pro Asp Ala Phe Ala Ile Val Glu Arg Ala Gln Gln
                355                 360                 365

Met Val Glu Ile Leu Thr Glu Glu Asn Arg Val Leu His Gln Glu Leu
                370                 375                 380

Gln Gly Cys Tyr Asp Asn Ala Asp Lys Leu His Lys Phe Glu Lys Glu
385                 390                 395                 400

Leu Gln Ser Ile Ser Glu Ala Tyr Glu Ser Leu Val Lys Ser Thr Thr
                405                 410                 415

Lys Arg Glu Ser Leu Asp Lys Ala Met Arg Thr Lys Leu Glu Gly Glu
                420                 425                 430

Ile Arg Arg Leu His Asp Phe Asn Arg Asp Leu Arg Asp Arg Leu Glu
                435                 440                 445

Thr Ala Asn Arg Gln Leu Ser Ser Arg Glu Tyr Asp Gly His Glu Asp
                450                 455                 460

Lys Ala Ala Glu Ser His Tyr Val Ser Gln Asn Lys Glu Phe Leu Lys
465                 470                 475                 480

Glu Lys Glu Lys Leu Glu Met Glu Leu Ala Ala Val Arg Thr Ala Ser
                485                 490                 495

Glu Asp His Arg Arg His Ile Glu Ile Leu Asp Gln Ala Leu Ser Asn
                500                 505                 510

Ala Gln Ala Arg Val Ile Lys Leu Glu Glu Glu Leu Arg Glu Lys Gln
                515                 520                 525

Ala Tyr Val Glu Lys Val Glu Lys Leu Gln Gln Ala Leu Thr Gln Leu
                530                 535                 540

Gln Ser Ala Cys Glu Lys Arg Gly Gln Met Glu Arg Arg Leu Arg Thr
545                 550                 555                 560

Trp Leu Glu Arg Glu Leu Asp Ala Leu Arg Thr Gln Gln Lys His Gly
                565                 570                 575

Thr Gly Pro Pro Val Ser Leu Pro Glu Cys Asn Ala Pro Ala Leu Met
                580                 585                 590

Glu Leu Val Arg Glu Lys Glu Glu Arg Ile Leu Ala Leu Glu Ala Asp
                595                 600                 605

Met Thr Lys Trp Glu Gln Lys Tyr Leu Glu Glu Ser Thr Ile Arg His
                610                 615                 620

Phe Ala Met Ser Ala Ala Ala Ala Thr Ala Glu Arg Asp Thr Thr
625                 630                 635                 640

Ile Ser Asn His Ser Arg Asn Gly Ser Tyr Gly Glu Ser Ser Leu Glu
                645                 650                 655

Ala His Ile Trp Pro Glu Glu Glu Val Val Gln Ala Asn Arg Arg
                660                 665                 670

Cys Gln Asp Met Glu Tyr Thr Ile Lys Asn Leu His Ala Lys Ile Ile
                675                 680                 685

Glu Lys Asp Ala Met Ile Lys Val Leu Gln Gln Arg Ser Arg Lys Asp
                690                 695                 700

Ala Gly Lys Thr Asp Ser Ala Ser Leu Arg Pro Ala Arg Ser Val Pro
705                 710                 715                 720

Ser Ile Ala Ala Ala Thr Gly Thr His Ser Arg Gln Thr Ser Leu Thr
                725                 730                 735
```

-continued

| | | | | | | | | | | | |
|---|---|---|---|---|---|---|---|---|---|---|---|
|Ser|Ser|Gln|Leu|Thr|Glu|Glu|Lys|Lys|Glu|Lys|Thr Thr Trp Lys|
| | | |740| | |745| | | |750| |

Gly Ser Ile Gly Phe Leu Leu Gly Lys Glu His Gln Gly Gln Ala Ser
           755                      760                      765

Ala Pro Leu Leu Pro Thr Thr Pro Ala Ser Ala Leu Ser Leu Pro Ala
        770                      775                      780

Ser Thr Thr Ser Ala Ser Ser Thr His Ala Lys Thr Gly Ser Lys Asp
785                      790                      795                      800

Ser Ser Thr Gln Thr Asp Lys Ser Thr Glu Leu Phe Trp Pro Ser Met
        805                      810                      815

Ala Ser Leu Pro Ser Arg Gly Arg Leu Ser Thr Ala Pro Ser Asn Ser
        820                      825                      830

Pro Ile Leu Lys His Pro Ala Ala Lys Gly Ala Val Glu Lys Gln Glu
        835                      840                      845

Asn Ser Pro Gly His Gly Lys Ala Ser Glu His Arg Gly Arg Val Ser
850                      855                      860

Asn Leu Leu His Lys Pro Glu Phe Pro Asp Gly Glu Met Met Glu Val
865                      870                      875                      880

Leu Ile

<210> SEQ ID NO 3
<211> LENGTH: 2319
<212> TYPE: DNA
<213> ORGANISM: Mus musculus
<220> FEATURE:
<221> NAME/KEY: CDS
<222> LOCATION: (1)..(2319)

<400> SEQUENCE: 3

```
atg agg aca ctg gaa gac tcc tca ggg aca gtc ctg cac cgt ctc atc      48
Met Arg Thr Leu Glu Asp Ser Ser Gly Thr Val Leu His Arg Leu Ile
 1               5                  10                  15 caa gag cag ctg cgc tac ggc aac ctg aca gag act cgc act ctg ctg      96
Gln Glu Gln Leu Arg Tyr Gly Asn Leu Thr Glu Thr Arg Thr Leu Leu
                20                  25                  30 gct atc cag cag cag gcc ctg cgg ggt ggg gct gga gct ggg ggc acg     144
Ala Ile Gln Gln Gln Ala Leu Arg Gly Gly Ala Gly Ala Gly Gly Thr
            35                  40                  45 ggg agc ccc cag gct tcc ttg gag atc gga gca ccc gag gac agt cag     192
Gly Ser Pro Gln Ala Ser Leu Glu Ile Gly Ala Pro Glu Asp Ser Gln
        50                  55                  60 gtg ctg cag caa gcc acc agg cag gag ccc cag ggc cag gag cat cag     240
Val Leu Gln Gln Ala Thr Arg Gln Glu Pro Gln Gly Gln Glu His Gln
 65                  70                  75                  80 ggt gga gag acc cac ctg gca gag aac agg ctg tac cgg ctg tgc cca     288
Gly Gly Glu Thr His Leu Ala Glu Asn Arg Leu Tyr Arg Leu Cys Pro
                 85                  90                  95 cag ccc agc aaa gga gaa gag ttg ccc acc tat gag gag gcc aaa gcc     336
Gln Pro Ser Lys Gly Glu Glu Leu Pro Thr Tyr Glu Glu Ala Lys Ala
                100                 105                 110 cat tcg cag tac tac gca gcg cag cag gca ggg tcc cgg ccg cat gtt     384
His Ser Gln Tyr Tyr Ala Ala Gln Gln Ala Gly Ser Arg Pro His Val
            115                 120                 125 ggg gac cgg gat cct aga gga ggg gtg tcc gga ggc ggc cgg cga cag     432
Gly Asp Arg Asp Pro Arg Gly Gly Val Ser Gly Gly Gly Arg Arg Gln
        130                 135                 140 gat gaa gct ctt cga gag ctg agg cat ggc cat gtg cgc tcc ttg agt     480
Asp Glu Ala Leu Arg Glu Leu Arg His Gly His Val Arg Ser Leu Ser
145                 150                 155                 160
```

```
gaa cgg ctt ctg caa ctg tcc ctg gaa aga aac ggt gct cgg gtc ccc      528
Glu Arg Leu Leu Gln Leu Ser Leu Glu Arg Asn Gly Ala Arg Val Pro
            165                 170                 175 agc cac atg agc tct tcc cac agc ttc cct cag ctg gcc cgc agc cag      576
Ser His Met Ser Ser Ser His Ser Phe Pro Gln Leu Ala Arg Ser Gln
        180                 185                 190 cag ggc ccc caa ccc cga ggg ccc cca gct gag ggc cca gag ccc cgc      624
Gln Gly Pro Gln Pro Arg Gly Pro Pro Ala Glu Gly Pro Glu Pro Arg
    195                 200                 205 ggg cca cca cct cag tac cca cac gct gta atg gct cag gag act gcg      672
Gly Pro Pro Pro Gln Tyr Pro His Ala Val Met Ala Gln Glu Thr Ala
210                 215                 220 gct gtc act gac cca aga tac cga ccc cga agc agc cca cac ttc cag      720
Ala Val Thr Asp Pro Arg Tyr Arg Pro Arg Ser Ser Pro His Phe Gln
225                 230                 235                 240 cat gcc gaa gtc agg atc ctg cag gcc cag gta cca ccg gtg ttc ctc      768
His Ala Glu Val Arg Ile Leu Gln Ala Gln Val Pro Pro Val Phe Leu
                245                 250                 255 cag cag cag cag tac cag tac ctg cca cag ccc cag gag cac tct cca      816
Gln Gln Gln Gln Tyr Gln Tyr Leu Pro Gln Pro Gln Glu His Ser Pro
            260                 265                 270 ccc ctc cac ccg gca gct ctg ggc cat gga ccc cca agc tcc ttt ggt      864
Pro Leu His Pro Ala Ala Leu Gly His Gly Pro Pro Ser Ser Phe Gly
        275                 280                 285 cca cct gca gtg gag gga cca ccc agt gcc cag gcc acc ttg ggc agt      912
Pro Pro Ala Val Glu Gly Pro Pro Ser Ala Gln Ala Thr Leu Gly Ser
    290                 295                 300 gcc cac ctg gcc cag atg gag act gta ctg agg gag aat gcc agg ctg      960
Ala His Leu Ala Gln Met Glu Thr Val Leu Arg Glu Asn Ala Arg Leu
305                 310                 315                 320 cag agg gac aat gag cga ttg cag aga gag ctg gag agc act tca gag     1008
Gln Arg Asp Asn Glu Arg Leu Gln Arg Glu Leu Glu Ser Thr Ser Glu
                325                 330                 335 aag gct ggc cgc ata gaa aag ctg gaa aat gaa atc cag cgg ctc tct     1056
Lys Ala Gly Arg Ile Glu Lys Leu Glu Asn Glu Ile Gln Arg Leu Ser
            340                 345                 350 gag gcc cac gag agc ctg atg agg acc tct tcc aag cgt gag gcc ctg     1104
Glu Ala His Glu Ser Leu Met Arg Thr Ser Ser Lys Arg Glu Ala Leu
        355                 360                 365 gag aag acc atg agg aac aag atg gac ggt gag atg aga cgg ttg cag     1152
Glu Lys Thr Met Arg Asn Lys Met Asp Gly Glu Met Arg Arg Leu Gln
    370                 375                 380 gac ttc aac cga gac ctt aga gag aga ttg gaa tcg gca aac cgc cac     1200
Asp Phe Asn Arg Asp Leu Arg Glu Arg Leu Glu Ser Ala Asn Arg His
385                 390                 395                 400 ctg gca agc aag acc cag gaa gcc cag gcg ggc agt cag gac atg gtg     1248
Leu Ala Ser Lys Thr Gln Glu Ala Gln Ala Gly Ser Gln Asp Met Val
                405                 410                 415 gcg aaa ctg ctt gcc cag agc tat gag cag caa cag gaa cag gag aag     1296
Ala Lys Leu Leu Ala Gln Ser Tyr Glu Gln Gln Gln Glu Gln Glu Lys
            420                 425                 430 ctg gag cgg gag atg gca ctg ctg cgt ggt gcc atc gag gac cag cgg     1344
Leu Glu Arg Glu Met Ala Leu Leu Arg Gly Ala Ile Glu Asp Gln Arg
        435                 440                 445 cga cat gct gaa ctg ctg gag cag gct ctg ggc aat gca caa agc cgt     1392
Arg His Ala Glu Leu Leu Glu Gln Ala Leu Gly Asn Ala Gln Ser Arg
    450                 455                 460 gcc gcc cgg gct gaa gag gag cta cgc aaa aag cag gcc tat gtg gag     1440
Ala Ala Arg Ala Glu Glu Glu Leu Arg Lys Lys Gln Ala Tyr Val Glu
```

```
                    -continued
465              470             475             480
aag gtg gag cgg ctg cag cag gca ctg ggg cag ttg cag gct gcc tgt     1488
Lys Val Glu Arg Leu Gln Gln Ala Leu Gly Gln Leu Gln Ala Ala Cys
                485             490             495 gaa aag cga gag cag ttg gag ctg cgt ctg cgc acg cgc ctg gag cag     1536
Glu Lys Arg Glu Gln Leu Glu Leu Arg Leu Arg Thr Arg Leu Glu Gln
            500             505             510 gaa ctc aaa gcc ttg cgt gca cag cag agg cag aca ggc acc ctc gca     1584
Glu Leu Lys Ala Leu Arg Ala Gln Gln Arg Gln Thr Gly Thr Leu Ala
        515             520             525 ggt ggt ggc ggc agc cat ggt ggg tcc gcc gag ctc agt gcc ctg cgg     1632
Gly Gly Gly Gly Ser His Gly Gly Ser Ala Glu Leu Ser Ala Leu Arg
    530             535             540 ctg tct gaa cag ctg cgg gag aag gag gaa cag atc ctg gct cta gag     1680
Leu Ser Glu Gln Leu Arg Glu Lys Glu Glu Gln Ile Leu Ala Leu Glu
545             550             555             560 gcg gac atg acc aag tgg gaa cag aag tat ttg gaa gaa cgg gct atg     1728
Ala Asp Met Thr Lys Trp Glu Gln Lys Tyr Leu Glu Glu Arg Ala Met
                565             570             575 agg cag ttc gcc atg gac gcg gct gcc act gcg gct gcc cag cgc gat     1776
Arg Gln Phe Ala Met Asp Ala Ala Ala Thr Ala Ala Ala Gln Arg Asp
            580             585             590 acc act ctc atc cgg cac tcc ccc cag ccc tcg ccc agc agc agt ttc     1824
Thr Thr Leu Ile Arg His Ser Pro Gln Pro Ser Pro Ser Ser Ser Phe
        595             600             605 aac gag ggc ctg ctg cca ggc aac cac agg cac cag gag atg gag agc     1872
Asn Glu Gly Leu Leu Pro Gly Asn His Arg His Gln Glu Met Glu Ser
    610             615             620 aga ttg aag gtg ctc cat gct cag atc cta gag aag gat gcg gtg atc     1920
Arg Leu Lys Val Leu His Ala Gln Ile Leu Glu Lys Asp Ala Val Ile
625             630             635             640 aag gtc ctt cag cag cgc tcc agg aaa gac cct ggc aag gcc acc cag     1968
Lys Val Leu Gln Gln Arg Ser Arg Lys Asp Pro Gly Lys Ala Thr Gln
                645             650             655 ggc acc cta cgg cct gcc aag tcg gtg ccg tcc atc ttc gcg gct gca     2016
Gly Thr Leu Arg Pro Ala Lys Ser Val Pro Ser Ile Phe Ala Ala Ala
            660             665             670 gtg gga act cag ggc tgg caa ggg ctc gta tcc agt gag cgg caa act     2064
Val Gly Thr Gln Gly Trp Gln Gly Leu Val Ser Ser Glu Arg Gln Thr
        675             680             685 gat gca cgg cca gcg gga gac cgg gtc cca gca gag gag cct ccg gcc     2112
Asp Ala Arg Pro Ala Gly Asp Arg Val Pro Ala Glu Glu Pro Pro Ala
    690             695             700 aca gct cct ctc cct gcc cac acc aaa cat ggc agc aga gac ggg agc     2160
Thr Ala Pro Leu Pro Ala His Thr Lys His Gly Ser Arg Asp Gly Ser
705             710             715             720 acc cag acg gat ggc cct gca gac aac acc tct gcc tgc ttg gcc tca     2208
Thr Gln Thr Asp Gly Pro Ala Asp Asn Thr Ser Ala Cys Leu Ala Ser
                725             730             735 gaa ccc gat ggc ctc ctg ggg tgc aac agt agc cag agg aca ccc tct     2256
Glu Pro Asp Gly Leu Leu Gly Cys Asn Ser Ser Gln Arg Thr Pro Ser
            740             745             750 ctg gac tct ata gct gca acc aga gtc cag gat ctg tca gac atg gta     2304
Leu Asp Ser Ile Ala Ala Thr Arg Val Gln Asp Leu Ser Asp Met Val
        755             760             765 gaa ata ctg atc tga                                                 2319
Glu Ile Leu Ile
    770
```

-continued

<210> SEQ ID NO 4
<211> LENGTH: 772
<212> TYPE: PRT
<213> ORGANISM: Mus musculus

<400> SEQUENCE: 4

Met Arg Thr Leu Glu Asp Ser Ser Gly Thr Val Leu His Arg Leu Ile
1               5                   10                  15

Gln Glu Gln Leu Arg Tyr Gly Asn Leu Thr Glu Thr Arg Thr Leu Leu
            20                  25                  30

Ala Ile Gln Gln Gln Ala Leu Arg Gly Gly Ala Gly Ala Gly Gly Thr
        35                  40                  45

Gly Ser Pro Gln Ala Ser Leu Glu Ile Gly Ala Pro Glu Asp Ser Gln
    50                  55                  60

Val Leu Gln Gln Ala Thr Arg Gln Glu Pro Gln Gly Gln Glu His Gln
65                  70                  75                  80

Gly Gly Glu Thr His Leu Ala Glu Asn Arg Leu Tyr Arg Leu Cys Pro
                85                  90                  95

Gln Pro Ser Lys Gly Glu Leu Pro Thr Tyr Glu Ala Lys Ala
            100                 105                 110

His Ser Gln Tyr Tyr Ala Ala Gln Ala Gly Ser Arg Pro His Val
        115                 120                 125

Gly Asp Arg Asp Pro Arg Gly Gly Val Ser Gly Gly Arg Arg Gln
    130                 135                 140

Asp Glu Ala Leu Arg Glu Leu Arg His Gly His Val Arg Ser Leu Ser
145                 150                 155                 160

Glu Arg Leu Leu Gln Leu Ser Leu Glu Arg Asn Gly Ala Arg Val Pro
                165                 170                 175

Ser His Met Ser Ser His Ser Phe Pro Gln Leu Ala Arg Ser Gln
            180                 185                 190

Gln Gly Pro Gln Pro Arg Gly Pro Pro Ala Glu Gly Pro Glu Pro Arg
        195                 200                 205

Gly Pro Pro Pro Gln Tyr Pro His Ala Val Met Ala Gln Glu Thr Ala
    210                 215                 220

Ala Val Thr Asp Pro Arg Tyr Arg Pro Arg Ser Ser Pro His Phe Gln
225                 230                 235                 240

His Ala Glu Val Arg Ile Leu Gln Ala Gln Val Pro Pro Val Phe Leu
                245                 250                 255

Gln Gln Gln Gln Tyr Gln Tyr Leu Pro Gln Pro Gln Glu His Ser Pro
            260                 265                 270

Pro Leu His Pro Ala Ala Leu Gly His Gly Pro Pro Ser Ser Phe Gly
        275                 280                 285

Pro Pro Ala Val Glu Gly Pro Pro Ser Ala Gln Ala Thr Leu Gly Ser
    290                 295                 300

Ala His Leu Ala Gln Met Glu Thr Val Leu Arg Glu Asn Ala Arg Leu
305                 310                 315                 320

Gln Arg Asp Asn Glu Arg Leu Gln Arg Glu Leu Glu Ser Thr Ser Glu
                325                 330                 335

Lys Ala Gly Arg Ile Glu Lys Leu Glu Asn Glu Ile Gln Arg Leu Ser
            340                 345                 350

Glu Ala His Glu Ser Leu Met Arg Thr Ser Ser Lys Arg Glu Ala Leu
        355                 360                 365

Glu Lys Thr Met Arg Asn Lys Met Asp Gly Glu Met Arg Arg Leu Gln
    370                 375                 380

-continued

```
Asp Phe Asn Arg Asp Leu Arg Glu Arg Leu Glu Ser Ala Asn Arg His
385                 390                 395                 400

Leu Ala Ser Lys Thr Gln Glu Ala Gln Ala Gly Ser Gln Asp Met Val
            405                 410                 415

Ala Lys Leu Leu Ala Gln Ser Tyr Glu Gln Gln Gln Gln Gln Glu Lys
        420                 425                 430

Leu Glu Arg Glu Met Ala Leu Leu Arg Gly Ala Ile Glu Asp Gln Arg
    435                 440                 445

Arg His Ala Glu Leu Leu Glu Gln Ala Leu Gly Asn Ala Gln Ser Arg
450                 455                 460

Ala Ala Arg Ala Glu Glu Leu Arg Lys Lys Gln Ala Tyr Val Glu
465                 470                 475                 480

Lys Val Glu Arg Leu Gln Gln Ala Leu Gly Gln Leu Gln Ala Ala Cys
                485                 490                 495

Glu Lys Arg Glu Gln Leu Glu Leu Arg Leu Arg Thr Arg Leu Glu Gln
            500                 505                 510

Glu Leu Lys Ala Leu Arg Ala Gln Gln Arg Gln Thr Gly Thr Leu Ala
        515                 520                 525

Gly Gly Gly Gly Ser His Gly Gly Ser Ala Glu Leu Ser Ala Leu Arg
    530                 535                 540

Leu Ser Glu Gln Leu Arg Glu Lys Glu Gln Ile Leu Ala Leu Glu
545                 550                 555                 560

Ala Asp Met Thr Lys Trp Glu Gln Lys Tyr Leu Glu Glu Arg Ala Met
                565                 570                 575

Arg Gln Phe Ala Met Asp Ala Ala Thr Ala Ala Ala Gln Arg Asp
            580                 585                 590

Thr Thr Leu Ile Arg His Ser Pro Gln Pro Ser Pro Ser Ser Ser Phe
        595                 600                 605

Asn Glu Gly Leu Leu Pro Gly Asn His Arg His Gln Glu Met Glu Ser
    610                 615                 620

Arg Leu Lys Val Leu His Ala Gln Ile Leu Glu Lys Asp Ala Val Ile
625                 630                 635                 640

Lys Val Leu Gln Gln Arg Ser Arg Lys Asp Pro Gly Lys Ala Thr Gln
                645                 650                 655

Gly Thr Leu Arg Pro Ala Lys Ser Val Pro Ser Ile Phe Ala Ala Ala
            660                 665                 670

Val Gly Thr Gln Gly Trp Gln Gly Leu Val Ser Ser Glu Arg Gln Thr
        675                 680                 685

Asp Ala Arg Pro Ala Gly Asp Arg Val Pro Ala Glu Glu Pro Ala
690                 695                 700

Thr Ala Pro Leu Pro Ala His Thr Lys His Gly Ser Arg Asp Gly Ser
705                 710                 715                 720

Thr Gln Thr Asp Gly Pro Ala Asp Asn Thr Ser Ala Cys Leu Ala Ser
                725                 730                 735

Glu Pro Asp Gly Leu Leu Gly Cys Asn Ser Ser Gln Arg Thr Pro Ser
            740                 745                 750

Leu Asp Ser Ile Ala Ala Thr Arg Val Gln Asp Leu Ser Asp Met Val
        755                 760                 765

Glu Ile Leu Ile
    770
```

<210> SEQ ID NO 5
<211> LENGTH: 32
<212> TYPE: DNA

```
<213> ORGANISM: Artificial Sequence
<220> FEATURE:
<223> OTHER INFORMATION: primer

<400> SEQUENCE: 5
cgcgtcgaca tgaggacact ggaagactcc tc                              32

<210> SEQ ID NO 6
<211> LENGTH: 35
<212> TYPE: DNA
<213> ORGANISM: Artificial Sequence
<220> FEATURE:
<223> OTHER INFORMATION: primer

<400> SEQUENCE: 6
gcggcggccg ctcagatcag tatttctacc atgtc                           32

<210> SEQ ID NO 7
<211> LENGTH: 33
<212> TYPE: DNA
<213> ORGANISM: Artificial Sequence
<220> FEATURE:
<223> OTHER INFORMATION: primer

<400> SEQUENCE: 7
cgcgtcgaca gcacggagct cttctggccc agc                             33

<210> SEQ ID NO 8
<211> LENGTH: 38
<212> TYPE: DNA
<213> ORGANISM: Artificial Sequence
<220> FEATURE:
<223> OTHER INFORMATION: primer

<400> SEQUENCE: 8
gcggcggccg cctagatgag cacttccatc atctcgcc                        38

<210> SEQ ID NO 9
<211> LENGTH: 32
<212> TYPE: DNA
<213> ORGANISM: Artificial Sequence
<220> FEATURE:
<223> OTHER INFORMATION: primer

<400> SEQUENCE: 9
cgcgtcgaca tgaggacact ggaagactcc tc                              32

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
cgcgtcgaca tgagaggttc tgaggatgta gcc                             33
```

US 7,129,063 B2

EXOCRINE GLAND TIGHT JUNCTION-CONSTITUTING PROTEIN JEAP FAMILY

This application claims the priority of Japanese Patent Application No. 2001-352241, filed Nov. 16, 2001 which is incorporated herein by reference in its entirety.

BACKGROUND OF THE INVENTION

The present invention relates to a novel component protein of tight junctions (hereinafter referred to as TJs) of exocrine glands and uses of the protein.

In multicellular animals, information on junction of adjacent cells is deeply related to control and maintenance of life phenomena such as proliferation and differentiation of cells, inflammation, and metastasis of cancers. In many cases, intercellular adhesion molecules that participate in adhesion gather on the surface of cells to form a membrane region uniquely differentiated for adhesion. In particular, in epithelial cells, it has been known that intercellular adhesion molecules such as cadherin are strongly bound to cytoskeleton in the cytoplasm domain.

Such a membrane region, which is called an intercellular adhesion mechanism, is generally classified into four types: gap junction (GJ), adherens junction (AJ), desmosome and tight junction (TJ).

TJ is one of intercellular adhesion mechanisms in the epithelial or endothelial cell layer. It plays a role of a physical barrier for preventing free passage of solutes and water through extracellular space (barrier function), and constitutes a continuous peripheral seal surrounding the cells. Also, it is considered that TJ plays a role of a boundary between apical and basolateral cytomembrane regions for forming and maintaining cell polarity (fence function).

TJs comprise transmembrane protein molecules such as claudin, occludin and JAM and peripheral membrane proteins, such as ZO-1, -2 and -3, cingulin, 7H6, symplekin, Rab3B, Sec6/Sec8 homolog, ASIP/PAR-3, PAR-6, and MAGI-1. Claudin and occludin constitute the backbone of TJ strands and are involved in the barrier function of TJs.

JAM is involved in cell-cell adhesion and/or junctional assembly of endothelial and epithelial cells, as well as infiltration of monocytes through interstices between endothelial cells induced by chemokines. ZO-1, -2 and -3 are scaffold proteins containing PDZ domains and directly bind to claudin and occludin at the cytoplasmic surface of TJ strands. ZO-1, -2 and -3 also bind to F-actin and might regulate TJ functions via cross-linking TJ strands and the actin cytoskeleton. Several other PDZ domains-containing proteins localized at TJs might also serve as landmarks to recruit cytoskeletal and signaling proteins to TJ strands. As a non-F-actin binding scaffold protein, MAGI-1/2/3 localizes at TJs and interacts with signaling molecules such as a tumor suppressor gene product, PTEN, and a GDP/GTP exchange protein for Rap small G protein. ASIP/PAR-3 and PAR-6 are cell polarity-related molecules containing PDZ domains and interact with a typical protein kinase C (PKC). ASIP/PAR-3 interacts with JAM. Among peripheral membrane proteins devoid of PDZ domains at TJ strands, Rab3B and Sec6/Sec8 homologs are involved in vesicular transport. Furthermore, cingulin, 7H6 antigen, and symplekin have been known to localize at TJs. However, their functions have not been elucidated yet. Cingulin interacts with ZO-1, -2 and -3, occludin, AF-6, and JAM.

To further characterize the molecular organization of TJ, identification and provision of novel TJ-constituting proteins has been desired.

Meanwhile, a mouse cDNA clone (GenBank accession No. BAB30287) has been reported by RIKEN as a gene whose function is unknown.

SUMMARY OF THE INVENTION

An object of the present invention is to provide a novel component protein of TJs in exocrine glands.

To clarify the details of molecular organization of intercellular adhesion, the inventors of the present invention have attempted to screen for novel proteins localized at cell-cell junctions by a fluorescence-labeled protein localization-based expression cloning method.

First, several cDNA fragments derived from mouse vascular endothelial cell line MS-1 cells were expressed as GFP fusion proteins, and a cDNA fragment that encodes a gene product localized at the cell-cell junctions was isolated based on observation of subcellular distribution of the fluorescence-labeled proteins. observed in exocrine glands such as pancreas, submandibular gland and lacrimal gland but not in small intestine.

From the above results, it has been found that JEAP and JEAP-2 form a gene family that constitutes TJs of exocrine glands, thereby achieving the present invention.

Therefore, the present invention relates to the following items.

1. A protein of the following (a) or (b):
   (a) a protein having an amino acid sequence shown in SEQ ID NO:4; and
   (b) a protein having an amino acid sequence having deletion, substitution or addition of one or several amino acids in an amino acid sequence shown in SEQ ID NO:2 or SEQ ID NO:4, and localizing at tight junctions, with a proviso that the protein is not a protein having an amino acid sequence shown in SEQ ID NO:2.
2. A DNA encoding the protein as defined in the item 1.
3. A DNA according to the item 2, having a nucleotide sequence shown in or SEQ ID NO:3.
4. A DNA of the following (a) or (b):
   (a) a DNA having a nucleotide sequence shown in SEQ ID NO:3; and
   (b) a DNA hybridizing with a DNA having a nucleotide sequence complementary to a nucleotide sequence shown in SEQ ID NO:1 or SEQ ID NO:3 under a stringent condition and encoding a protein localizing at tight junctions, with a proviso that the DNA is not a DNA having a nucleotide sequence shown in SEQ ID NO:1.
5. A DNA of the following (a) or (b):
   (a) a DNA having a nucleotide sequence shown in SEQ ID NO:3; and
   (b) a DNA having a nucleotide sequence with 90% or more homology to a nucleotide sequence shown in SEQ ID NO:1 or SEQ ID NO:3 and encoding a protein localizing at tight junctions,
   with a proviso that the DNA is not a DNA having a nucleotide sequence shown in SEQ ID NO:1.
6. A protein encoded by the DNA as defined in the item 4 or 5.
7. A recombinant vector comprising the DNA as defined in any one of the items 2 to 5.
8. A transformant obtained by transforming a host with the DNA as defined in any one of the items 2 to 5.
9. A method for producing a protein localizing at tight junctions, comprising:

culturing the transformant as defined in the item 8; and collecting a protein localizing at tight junctions expressed by the transformant from the culture.

10. An antibody reacting with the protein as defined in the item 1.

11. A method for measuring the protein as defined in the item 1, comprising using the antibody as defined in the item 10 to measure the protein.

12. A method for measuring a DNA or RNA encoding the protein as defined in the item 1, comprising using an oligonucleotide having a nucleotide sequence composed of at least 15 consecutive nucleotides in a nucleotide sequence shown in SEQ ID NO:1 or SEQ ID NO:3 as a primer or probe to measure the DNA or RNA.

13. A method for screening for a substance having a reactivity with the protein as defined in the item 1 or a protein having an amino acid sequence shown in SEQ ID NO:2, comprising the steps of:
(1) mixing the protein as defined in the item 1 or the protein having the amino acid sequence shown in SEQ ID NO:2, or a partial peptide thereof with a test substance; and
(2) measuring an amount of the test substance bound or not bound to the protein as defined in the item 1 or the protein having the amino acid sequence shown in SEQ ID NO:2, or the partial peptide thereof, thereby screening for the substance.

14. A method for screening for a substance affecting expression of the protein as defined in the item 1 or a protein having an amino acid sequence shown in SEQ ID NO:2, comprising the steps of:
(1) culturing a cell expressing the protein as defined in the item 1 or the protein having the amino acid sequence shown in SEQ ID NO:2 in the presence of a test substance; and
(2) measuring the protein as defined in the item 1 or the protein having the amino acid sequence shown in SEQ ID NO:2 expressed in the cell or mRNA encoding the protein as defined in the item 1 or the protein having the amino acid sequence shown in SEQ ID NO:2 in the cell, thereby screening for the substance.

15. A method for screening a substance affecting expression of the protein as defined in the item 1 or a protein having an amino acid sequence shown in SEQ ID NO:2, comprising the steps of:
(1) identifying a promoter region controlling expression of the protein as defined in item 1 or the protein having the amino acid sequence shown in SEQ ID NO:2; and
(2) measuring an influence of a test substance on a promoter activity of the promoter region, thereby screening for the substance.

16. A method for screening for a substance affecting distribution of the protein as defined in the item 1 or the protein having the amino acid sequence shown in SEQ ID NO:2, comprising the steps of:
(1) culturing a cell expressing the protein as defined in the item 1 or the protein having the amino acid sequence shown in SEQ ID NO:2 in the presence of a test substance; and
(2) measuring distribution of the protein as defined in claim 1 or the protein having the amino acid sequence shown in SEQ ID NO:2 in the cell, thereby screening for the substance.

DETAILED DESCRIPTION OF THE INVENTION

Figure 1:
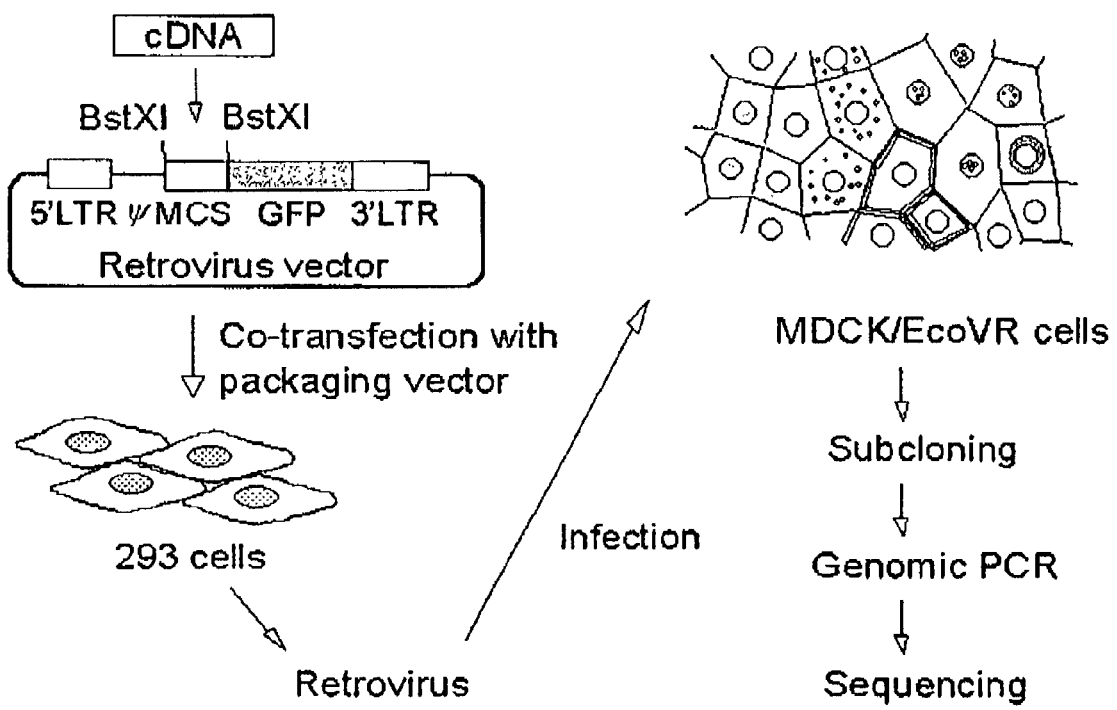
FIG. 1 is a schematic representation of cDNA cloning for a protein localized at an intercellular adhesion site.

Hereinafter, the present invention will be described in detail. For convenience's sake, the protein which is revealed by the present inventors that they localize at tight junctions, including the protein having the amino acid sequence shown in SEQ ID NO:2, are referred to as "the protein of the present invention".

Of the proteins of the present invention, those proteins having the amino acid sequence shown in SEQ ID NO:2 or 4 are proteins identified as ones localized at tight junctions, as will be described in Examples below. Generally, proteins are expected to have mutants having the identical function and appropriate modification of the amino acid sequence of a protein can give rise to a mutant having the identical function. Therefore, those proteins that have an amino acid sequence having deletion, substitution or addition of one or more amino acids in the amino acid sequence shown in SEQ ID NO:2 or SEQ ID NO:4 and that localize at tight junctions are also encompassed by the proteins of the present invention.

The modification of the amino acid sequence of a protein can be performed by modifying the nucleotide sequence of DNA encoding the protein by a well-known means such as site-specific mutation inducing method and expressing the DNA having the modified nucleotide sequence. One skilled in the art can readily confirm localization of the protein at tight junctions by means of, for example, a fluorescent antibody technique or immuno-electron microscopy.

The protein of the present invention may be converted into fused proteins by fusing it with other proteins such as glutathione transferase (GST) or His tag.

The DNA of the present invention is a DNA that encodes the protein of the present invention. The DNA of the present invention includes DNA having a nucleotide sequence shown in SEQ ID NO:1 or SEQ ID NO:3. The DNA was one whose nucleotide sequence was determined in Examples described below. Generally, for a gene, there are expected to exist genes that encode the same product but have different nucleotide sequences or genes that encode mutants having the same function as that of the gene concerned. Also, modification of the nucleotide sequence of the gene can give rise to a gene that encodes a mutant producing the same product or exhibiting the same function as that of the gene concerned. Therefore, the DNA of the present invention encompasses DNAs having nucleotide sequences similar to that of SEQ ID NO:1 or SEQ ID NO:3 and encoding proteins localized at tight junctions. DNAs having similar nucleotide sequences include DNAs that hybridize with a DNA having a nucleotide sequence complementary to that of SEQ ID NO:1 or SEQ ID NO:3 under a stringent condition and DNAs having nucleotide sequences with 90% or more homologies to the nucleotide sequence shown in SEQ ID NO:1 or SEQ ID NO:3.

Here, the term "stringent condition" comprises, for example, hybridization at 65° C. in 4×SSC followed by washing at 65° C. for 1 hour in 0.1×SSC. As an alternative method, the stringent condition comprises 42° C. in 4×SSC in 50% formamide. Also, conditions of performing hybridization at 65° C. for 2.5 hours in Perfect Hyb™ (TOYOBO), followed by washings 1) 2×SSC, 0.05% SDS solution: 25° C., 5 minutes, 2) 2×SSC, 0.05% SDS solution: 25° C., 15 minutes, and 3) 0.1×SSC, 0.1% SDS solution: 50° C., 20 minutes may be used.

The homology as used herein is the homology calculated by the Clustal W method.

Whether a DNA encodes protein localizing at tight junctions may be easily confirmed by expressing the DNA in a suitable cell which can form tight junctions, and determining the presence of the expressed protein in tight junctions by a fluorescent antibody technique, immuno-electron microscopy and the like as described above.

The DNA of the present invention can be used in the analysis of the gene of JEAP family protein and in the analysis of the expression of genes, by using a part of it as a primer or a probe. By the term "a part" is meant that the oligonucleotide used as a primer or a probe comprises a polynucleotide having a nucleotide sequence composed of at least consecutive 15 bases, preferably at least 20 bases, and more preferably at least about 20 to 30 bases corresponding to the DNA sequence of the present invention. As a probe, polynucleotides having larger molecular weights and whole DNA may also be used.

The DNA of the present invention can be obtained by a conventional method based on the revealed nucleotide sequence. For example, it can be synthesized by a chemical synthesis method, or by means of mRNA prepared from cells or tissues expressing the protein localized at the tight junction of the present invention or by an RT-PCR method.

The gene manipulation can be performed by the method described in the literature (Maniatis, et al., Molecular Cloning: A Laboratory Manual, Cold Spring Harbor Laboratory, 1989).

The vector of the present invention is a recombinant vector comprising the DNA of the present invention. The vector of the present invention may be obtained by inserting the DNA of the present invention into a vector such as an expression vector.

The transformant of the present invention is a transformant that can be obtained by transforming a host with the DNA of the present invention and expresses the protein of the present invention. The host is not particularly limited and includes animal cells, bacteria cells, yeast cells, insect cells, and the like. The transformation may be performed by a conventional method. For example, it may be performed by introduction into a host, of the vector of the present invention which expresses the protein of the present invention in the host.

The production method of the present invention is a method for producing the protein localized at the tight junction of the present invention. The method includes culturing the transformant of the present invention and collecting the protein expressed by the transformant and localized at the tight junction from the culture.

The culture may be performed under the condition where the transformant expresses the protein of the present invention. The collection of the protein of the present invention from the culture may be performed by appropriate combinations of various chromatographies, electrophoreses, gel filtrations and the like that have been usually used for the purification of proteins. In the case where the protein of the present invention is to be expressed as a fused protein with a tag such as GST or His tag, the protein can be purified by using a glutathione Sepharose column or a nickel Sepharose column, respectively.

The whole or a part of the JEAP protein of the present invention can be used as an epitope for preparing antibodies, which in turn can be used as reagents for investigation and diagnosis. By the term "epitope" is meant an antigenic determinant of a polypeptide, which generally comprises at least six amino acids. It is known that polypeptides composed of six amino acids bind with antibodies (JP-60-500684 A). The antigenic peptide of the protein of the present invention means a polypeptide composed of at least six consecutive amino acids, preferably at least eight consecutive amino acids, more preferably at least about. 15 consecutive amino acids, and still more preferably at least about 20 consecutive amino acids based on the amino acid sequence of the present invention.

The antibody of the present invention can be obtained from animals immunized with the protein of the present invention obtained by the production method of the present invention or an antigenic peptide thereof. Polyclonal antibodies can be prepared from sera of the immunized animals while monoclonal antibodies can be prepared by fusing antibody-producing cells obtained from the spleen or lymph nodes of the immunized animals with myeloma cells and screening hybridomas producing antibodies showing strong specificity to the protein of the present invention.

As the immunogen, the protein of the present invention obtained by the production method of the present invention can be used. As an alternative method, the immunogen may be a fragment or peptide having a partial structure appropriately selected from amino acid sequences shown in SEQ ID NO:2 or SEQ ID NO:4. A complex between an antigen and a carrier protein can be prepared by using various coupling agents. For example, glutaraldehyde, carbodiimide, maleimide active ester, and the like can be used. The carrier protein may be those conventionally used such as bovine serum albumin, thyroglobulin, and hemocyanin. Usually, a method is used in which the carrier protein is coupled with the antigen in a proportion of 1- to 5-fold amount.

The animals to be immunized include mice, rats, rabbits, guinea pigs, hamsters and the like. The inoculation method includes subcutaneous, intramuscular and intraperitoneal administrations. Upon the administration, the complex may be mixed with Freund's complete adjuvant or Freund's incomplete adjuvant before it can be administered. The administration is performed usually once in 2 to 5 weeks. The antibody-producing cells obtained from the spleen or lymph node of the immunized animal are subjected to cell fusion with myeloma cells and isolated as hybridomas. As the myeloma cells, those derived from mice, rats, humans and the like are used. They are preferably derived from the same species as the antibody-producing cells but in some cases the immunization is possible between different species.

The procedures of cell fusion can be practiced by a known method, for example, a method of Kohler, G. and Milstein, C., Nature 256, 495, 1975. The fusion accelerator includes polyethylene glycol, Sendai virus and the like. The cell fusion can be usually practiced by reacting the cells at 20 to 40° C., preferably at 30 to 37° C. for about 1 to 10 minutes in a ratio of the number of antibody-producing cells to that of the myeloma cells of usually about 1:1 to about 10:1 by using polyethylene glycol (average molecular weight: 1,000 to 4,000) in a concentration of usually about 20 to 50%.

Various immunochemical methods can be used for the screening of antibody-producing hybridomas. The immunochemical methods include, for example, an ELISA (enzyme-linked immunosorbent assay) method using a microplate having coated thereon the protein of the present invention, an EIA (enzyme immunoassay) method using a microplate having coated thereon an anti-immunoglobulin antibody, an immunoblot method using a nitrocellulose transfer membrane after electrophoresing a sample containing the protein of the present invention, and the like.

Further cloning from such wells may be performed, for example, by a limiting dilution method to obtain a clone. Screening and breeding of hybridomas are performed in a medium for animal cells (for example, RPMI1640), usually containing HAT (hypoxanthine, aminopterin, thymidine) through addition and 10 to 20% fetal calf serum. The clone thus obtained can be transplanted into abdominal cavity of an SCID mouse preliminarily administered with pristane and the ascites containing a monoclonal antibody in a high concentration is collected therefrom after 10 to 14 days to obtain a raw material for purifying antibody. Also, the clone can be cultured and the culture may be used as a raw material for purifying antibody. The recovery of monoclonal antibody may be achieved without difficulty by using a known method as a purification method for immunoglobulins, for example, an ammonium sulfate fractionation method, a PEG fractionation method, an ethanol fractionation method, use of an anion exchange member, and further affinity chromatography and other means.

By using the antibody of the present invention, the protein of the present invention can be measured. The measurement can be performed by a conventional method using an antibody. For example, by the immunological method using the antibody (preferably monoclonal antibody) of the present invention, qualitative and quantitative determination of the protein of the present invention in biological samples can be performed. As the immunological method, a known method such as an immune tissue stain method, an enzyme immunoassay, an agglutination method, a competitive method, or a sandwich method may be applied to samples obtained by subjecting biological samples to appropriate treatment, for example, separation of cells, extraction operation or the like, as necessary. The immune tissue stain method can be performed, for example, by a direct method using a labeled antibody, and an indirect method using a labeled antibody against the antibody. As the labeling agent, any known labeling substances, such as fluorescent substances, radioactive substances, enzymes, metals, and dyestuffs can be used.

The antibody of the present invention may be used in the form of Fab' or Fab fraction free of Fc' or Fc region or polymers thereof. Alternatively, the antibody of the invention may be a chimera antibody or a humanized antibody thereof.

The screening for a substance such as a compound (such as drug) that affects the expression of the protein of the present invention can be practiced by culturing a cell expressing the protein of the present invention in the presence of a test substance, and then measuring the protein of the present invention expressed in the cell or mRNA encoding the protein in the cell.

The cell that expresses the protein of the present invention may be selected by Northern blotting, RT-PCR or the like. Also, the cell line may be selected by a fluorescent antibody technique, an enzyme antibody method or the like using the antibody obtained by the method described above.

The selected cell is cultured in the presence of a test substance (for example, the cell is cultured by adding a test substance to the cell) and then the mRNA expression amount is determined by Northern blotting, slot blot hybridization, RT-PCR, and the like, or the protein expression amount is determined by fluorescent antibody technique, an enzyme antibody method, and the like, thereby measuring the influence of the test substance on the expression of the protein of the present invention. For example, this can be done in accordance with the methods described in Example 3 and Example 6.

Furthermore, in order to enable screening of a large number of kinds of test subsntaces more readily, a promoter region controlling expression of the protein of the invention may be identified and then an influence of a test substance on a promoter activity may be measured.

The identification of the promoter region and the measurement of the influence of the test substance on the promoter activity may be performed as follows. A clone that hybridizes with the 5'-region of cDNA encoding the protein of the present invention is selected out of a human DNA library and is inserted into an appropriate promoter screening system to select a clone having a promoter activity. In some cases, the region indispensable for the promoter activity may be narrowed.

The DNA selected here that has a promoter region for the protein of the present invention is inserted on the upstream side of the DNA encoding an enzyme whose activity can be readily measured, such as luciferase or alkaline phosphatase, to construct a reporter gene. The reporter gene is introduced into a cell, for example, HeLa cell, that can be cultured together with a suitable resistant gene, such as Neo$^r$ or hyg$^r$ and the cells are selected with a substance corresponding to the resistant gene to establish a cell line enabling measurement of the activity of the promoter that expresses the protein of the present invention. By causing the substance to act on the cell line, the activity of the introduced enzyme is measured, thereby practicing screening for the substance that affects the expression of the protein of the present invention.

The protein of the present invention can be used as another screening system for selecting a substance that affects the intracellular localization or distribution of the protein of the present invention. The screening may be performed by culturing a cell expressing the protein of the present invention in the presence of a test substance and measuring distribution of the protein of the present invention in the cell.

An example of the screening method includes staining the cell line that expresses the protein of the present invention or transformant of the present invention by a fluorescent antibody technique, an enzyme antibody method or the like by using the antibody obtained by the above-mentioned method and observing the stained cells under a microscope to measure the influence of the test substance on the intracellular localization of the protein of the present invention. For example, this can be performed in accordance with the methods described in Example 3 and Example 6.

Furthermore, the protein of the present invention can be used as still another screening system for selecting a substance that binds to the protein of the present invention (that is, a substance having a reactivity with the protein of the present invention). The screening may be performed by mixing the protein of the present invention or a partial peptide thereof with a test substance, and measuring an amount of the test substance bound or not bound to the protein or the partial peptide thereof.

In this system, because the substance having reactivity with the protein of the present invention is considered to bind to a part of the protein of the present invention, a partial peptide of the protein of the present invention may be used. Therefore, the partial peptide is sufficient to have such a part that binding to the partial peptide becomes equivalent to binding to the protein of the present invention.

Also, the protein of the present invention may be in a form in which the protein is expressed in cell membrane of the transformant of the present invention. Therefore, mixing the protein of the present invention with the test substance includes mixing the transformant of the present invention or cell membrane thereof with the test substance.

The measurement of the test substance bound or not bound to the protein of the present invention or the partial peptide thereof may be performed by reacting the protein of the present invention and a test substance under appropriate conditions and determine presence or absence of the binding between the two. The determination can be performed by using, for example, a labeling substance as necessary.

Since the substance having reactivity with the protein of the present invention have a possibility that they affects the function of the protein of the present invention and there is observed exocrine specificity in distribution of the protein of the present invention as described in Examples, it is expected that substances having specificity to binding ability to the protein of the present invention have a possibility that they exhibit an organ-specific action.

Note that although the JEAP family whose structure has been actually analyzed by the present invention is derived from a mouse, the method of analyzing JEAP family gene and method of screening it of the invention are also encompassed by the scope of the present invention when human-derived JEAP family is used.

EXAMPLES

The present invention will be described in more detail by the following examples. However, the present invention should not be considered as being limited thereto. The antibodies and cells used in Examples were as follows. Rat anti-mouse JEAP monoclonal antibody and rat anti-mouse JEAP-2 monoclonal antibody were prepared by a conventional method by immunizing a rat with GST-JEAP fused protein containing amino acid sequence 808-882 (amino acid numbers in SEQ ID NO:2) of JEAP and GST-JEAP-2 fused protein containing amino acid sequence 726-772 (amino acid numbers in SEQ ID NO:4) of JEAP-2, respectively. Rabbit anti-ZO-1 polyclonal antibody, rabbit anti-claudin polyclonal-antibody, mouse anti-ZO-1 monoclonal antibody, and mouse anti-occludin monoclonal antibody were purchased from Zymed, Inc. Mouse anti-E-cadherin monoclonal antibody was purchased from Takara Shuzo Co., Ltd.

MDCK cells (Madin-Darby canine kidney cells) were cultured in a DMEM medium with 10% fetal calf serum (FCS). Mouse vascular endothelial cell line MS-1 was purchased from American Type Culture Collection (ATCC) and cultured in DMEM/5% FCS.

Example 1

Identification of cDNAs Encoding Proteins Localized at Intercellular Adhesion Site To further characterize the molecular organization of intercellular adhesion, identification of novel cDNAs encoding proteins localized at cell-cell junctions was attempted by the localization-based expression cloning method using a fluorescence-labeled protein (FIG. 1) of Kitamura et al. (Misawa, K. et al., Proc. Natl. Acad. Sci. USA 97, 3062-3066, 2000).

First, a pilot experiment was carried out in which an expression recombinant retrovirus expressing a fused protein between VE-cadherin localized at cell-cell junctions and a fluorescence protein EGFP was infected to various cell lines and fluorescent stained images were observed under a fluorescence microscope. As a result, no cell line that showed a clear fluorescent signal as viewed with naked eye existed so far as was examined. Accordingly, it was attempted to make MDCK cells having high cell height and showing clear cell-cell junctions competent for ecotropic retrovirus and use the competent cells in experiments. The ecotropic retrovirus competent MDCK cell (MDCK/EcoVR) was obtained as follows. The ecotropic virus receptor (EcoVR) cDNA was inserted into pCAGGS-puro and it was transfected to the MDCK cells by using LipofectAMINE reagent (Life Technologies, Inc.). After 24 hours, culture of the cells in the presence of 5 μg/ml of puromycin was started and resistant clones were selected. Each clone was isolated and infected with pMXII-EGFPN expression recombinant retrovirus and a high competent clone was obtained. EcoVR cDNA and pMX expression vector were kindly provided by Dr. T. Kitamura (Tokyo University, Tokyo, Japan). Transfection of VE-cadherin-EGFP expression recombinant retrovirus to MDCK/EcoVR cells gave rise to bright fluorescent signals, which indicated that the cell line was suitable for visual screening of proteins localized at cell-cell junctions.

A cDNA-GFP fusion library was created from a mouse endothelial cell line MS-1 based on a method of Kitamura et al. The resulting library contained $3 \times 10^5$ independent clones and showed an average insert size of cDNA with 1,500 bp. The expression library was then co-transfected into 293/EBNA-1 cells (Invitrogen Corporation) with a virus packaging vector, pCL-Eco (Imgenex Corporation), by using TransIT LT1 (Mirus Corporation) to prepare a recombinant retrovirus. MDCK/EcoVR cells were infected with variously diluted retrovirus supernatants to obtain singly infected cells. The initial frequency of the EGFP-positive cells was about 4% as determined by fluorescence-activated cell sorting (FACS) analysis. After culture, EGFP-positive cells were sorted by a cell sorter and cultured at 50 cells per well in 96 well plates. When the cells became confluent, screening of 10 plates was performed under a fluorescent microscope and there were selected 6 wells containing cells with junction-specific fluorescence of EGFP. These cells were replated into 10-cm dishes and a single clone was obtained. Each clone was expanded in 24-well plates, and cDNA integrated into the chromosome was recovered by PCR from the genomic DNA. Among the cDNAs encoding proteins showing the junction-specific staining pattern, a novel cDNA encoding protein unknown to be localized at cell-cell junctions was obtained.

Example 2

Cloning of Full-Length cDNA Encoding Mouse JEAP and JEAP-2

Using the cDNA fragment obtained in Example 1 as a probe, cDNA was cloned from a mouse MS-1 cell-derived cDNA library. The cloning of cDNA was performed as follows. The total RNA of mouse MS-1 cell was extracted with Trizol (Life Technologies, Inc.) and poly A(+) RNA was prepared with oligo dT beads (Miltenyi Biotec GmbH). The cDNA library was prepared based on this poly A (+)RNA with a Superscript II cDNA synthesis kit (Life Technologies, Inc.) and a PMXII vector and used for screening cDNAs. The nucleotide sequences were determined by use of Dye Terminator Cycle Sequence Kit (Applied Biosystems, Inc.). The detail of the cloning is described in (1) below. A protein encoded by the obtained cDNA was named JEAP.

Homology search using an amino acid sequence deduced from JEAP cDNA revealed that human cDNA clone KIAA0989 has homology thereto over the full length thereof. This clone has been reported by Kazusa DNA Research Institute as a gene whose function is unknown. Further, as a result of homology search using an amino acid sequence deduced from KIAA0989 cDNA, mouse EST clone (BF536192) and mouse cDNA clones (AF175967, AF175968) were identified to be partially homologous to each other. Using these nucleotide sequences, another cDNA was separated from mouse MS-1 cell cDNA. Single strand cDNA was prepared with Superscript II reversetranscriptase (Life Technologies, Inc.) based on the poly A (+)RNA of MS-1 cell and used for PCR. The nucleotide sequence of it was determined by use of Dye Terminator Cycle Sequence Kit (Applied Biosystems, Inc.). The detail of the cloning is described in (2) below. A protein encoded by the obtained cDNA was named JEAP-2.

(1) Determination of cDNA of JEAP

Figure 2:
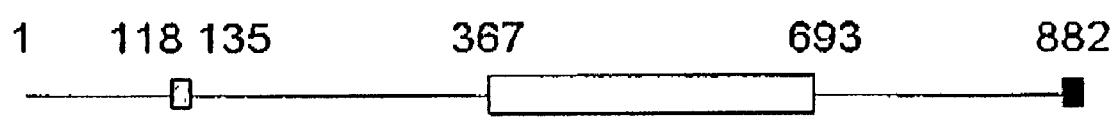
FIG. 2 is a schematic diagram showing structural features of JEAP and JEAP-2, respectively, with polyglutamic acid repeat being indicated by a shaded box, a coiled-coil domain being indicated by an open box, and a domain resembling the consensus motif of proteins binding to a PDZ domain being indicated by a filled box.
Figure 2:

A digoxigenin (DIG)-labeled probe was prepared by PCR by using the cDNA fragment obtained in Example 1 as a template and used for screening a pMXII MS-1 cell cDNA library. As a result, a plurality of positive clones were obtained, from which the nucleotide sequences of clones #2 and #5 were determined. As a result of structural analysis by determining the nucleotide sequence of the part including the entire open reading frame (ORF), JEAP cDNA contained ORF encoding a polypeptide with 882 amino acids with a calculated molecular weight of 98.4 kD (SEQ ID NO:1). JEAP contained a polyglutamic acid repeat at the N-terminal region, a coiled-coil domain at the middle region and a consensus motif for binding to PDZ domains at the C-terminal region (FIG. 2B).

RIKEN (the Institute of Physical and Chemical Research) reported the same mouse cDNA clone (BAB30287) as JEAP to be a gene with unknown functions.

(2) Determination of cDNA of JEAP-2

A structural correlation search on Genbank/EMBL/DDBJ database resulted in identification of homology between human cDNA clone KIAA0989 and JEAP over the full length thereof. Furthermore, homology search using the amino acid sequence deduced from KIAA0989 cDNA identified mouse EST clone (BF536192) and mouse cDNA clones (AF175967, AF175968) to be partially homologous to each other. Then, a cDNA containing the entire ORF was amplified from MS-1 cell cDNA by a PCR method by use of two kinds of primers of nucleotide sequences shown in SEQ ID NO:5 and SEQ ID NO:6 designed based on these mouse sequences. The cDNA was subcloned to pSPORT1 vector (Life Technology, Inc.) and it was named PSPORT-JEAP-2. Nucleotide sequence analysis indicated that cDNA of JEAP-2 contained ORF encoding a polypeptide with 772 amino acids having a calculated molecular weight of 85.3 kD (SEQ ID NO:3). The JEAP-2 polypeptide showed a high similarity to the sequence of JEAP (42% identity on the level of amino acid sequence). Structural analysis suggested that JEAP-2, like JEAP, contains a sequence containing a coiled-coil domain at the middle region, a consensus motif for binding to PDZ domains at the C-terminal region.

Example 3

Preparation of Monoclonal Antibody to Mouse JEAP and JEAP-2

A monoclonal antibody to mouse JEAP was prepared as follows. First, a region encoding the amino acid sequence 808–882 (amino acid number in SEQ ID NO:2) of JEAP was amplified by PCR using the clone #2 obtained in Example 2 as a template and oligonucleotides of nucleotide sequences shown in SEQ ID NO:7 and SEQ ID NO:8 as primers and introduced into GST fusion protein expressing vector (Amersham) and MBP fusion protein expressing vector (NEB) to express recombinant proteins. The GST-JEAP fusion protein was mixed with an adjuvant and a WKY rat was immunized therewith. Lymphocytes were isolated from the immunized rat and mixed with P3 myeloma cells in a mixing ratio of 1:5 (myeloma/lymphocyte), followed by cell fusion using PEG 1,500 solution (Boehringer) to prepare hybridomas. The prepared hybridomas were cultured in a 96-well plate for 1 week and the supernatant was assayed by ELISA with an ELISA plate having immobilized thereon MBP-JEAP fusion protein to identify positive wells. The hybridomas contained in the positive wells were cloned and finally a rat anti-mouse JEAP monoclonal antibody was obtained.

The rat anti-mouse JEAP-2 monoclonal antibody was prepared in the same manner as the JEAP monoclonal antibody. That is, a region encoding the amino acid sequence 726–772 (amino acid number in SEQ ID NO:4) of JEAP-2 was amplified by PCR using the pSPORT-JEAP-2 obtained in Example 2 as a template and oligonucleotides of nucleotide sequences shown in SEQ ID NO:6 and SEQ ID NO:9 as primers and introduced into GST fusion protein expressing vector (Amersham) and MBP fusion protein expressing vector (NEB) to prepare recombinant proteins. The GST-JEAP-2 fusion protein was mixed with an adjuvant and a WKY rat was immunized therewith. Lymphocytes were isolated from the immunized rat and mixed with P3 myeloma cells in a mixing ratio of 1:5 (myeloma/lymphocyte), followed by cell fusion using PEG 1,500 solution (Boehringer) to prepare hybridomas. The prepared hybridomas were cultured in a 96-well plate for 1 week and the supernatant was assayed by ELISA with an ELISA plate having immobilized thereon MBP-JEAP-2 fusion protein to identify positive wells. The hybridomas contained in the positive wells were cloned and finally a rat anti-mouse JEAP-2 monoclonal antibody was obtained.

Example 4

Expression and Intracellular Distribution of Mouse JEAP and JEAP-2

Whether the isolated cDNA clones contain the entire ORFs of JEAP and JEAP-2, respectively, was confirmed as follows by using the monoclonal antibody prepared in Example 3.

First, to prepare a JEAP expressing vector (pMXII JEAP IRES EGFP), the entire ORF of JEAP was amplified by PCR using oligonucleotides of nucleotide sequences shown in SEQ ID NO:8 and SEQ ID NO:10 as primers. SalI-NotI fragment of the PCR product was introduced into the SalI-NotI site of PMXII IRES EGFP to construct pMXII JEAP IRES EGFP. A JEAP-2 expressing vector, pMXII JEAP-2 IRES EGFP, was constructed by excising a SalI-NotI fragment containing the entire ORF of JEAP-2 from pSPORT1-JEAP-2 and introducing it into the SalI-NotI site of PMXII IRES EGFP.

The expression vector was transfected to 293/EBNA-1 cells (Invitrogen Corporation) by use of TransIT LT1 (Mirus Corporation). As SDS polyacrylamide electrophoresis, one-dimensional SDS-PAGE was performed in accordance with the method of Laemmli (1970), followed by immunoblotting, which was performed as follows. After transfer from the gel to a nitrocellulose membrane, the expressed protein was reacted with an antibody and the bound antibody was detected with peroxidase-labeled second antibody (Amersham) and ECL (Amersham) as a substrate for the enzyme.

A single band of 105-kDa was detected by Western blotting with an anti-JEAP monoclonal antibody in the extract of 293/EBNA-1 cells transfected with JEAP expressing vector, but not in that from nontransfected 293/EBNA-1 cells. The apparent molecular weight of the expressed JEAP was identical with that of JEAP endogenously expressed in MS-1 cells. Therefore, it revealed that the isolated cDNA contain the full-length of JEAP. Similarly, a single band of 105 kDa was detected by Western blotting with an anti-JEAP-2 monoclonal antibody in the extracts of 293/EBNA-1 cells transfected with JEAP-2 expressing vector. In the extracts of nontransfected 293/EBNA-1 cells, a thin band that is thought to be derived from endogenous JEAP-2 was contain. The apparent molecular weight of the expressed JEAP-2 was identical with that of JEAP-2 endogenously expressed in 293/EBNA-1 cells. Therefore, it revealed that the isolated cDNA contain the entire ORF of JEAP-2.

Next, to examine expression and distribution of mouse JEAP and JEAP-2, JEAP and JEAP-2 were each expressed in MDCK/EcoVR cells and the cells were stained with a monoclonal antibody.

The expressing vector was cotransfected together with virus packaging vector pCL-Eco (Imgenex Corporation) to 293/EBNA-1 cells (Invitrogen Corporation) by use of TransIT LT1 (Mirus Corporation) to prepare a recombinant retrovirus. The recombinant virus was transfected to MDCK/EcoVR cells to obtain MDCK/EcoVR cells stably expressing JEAP or JEAP-2. The JEAP-expressing cells were confirmed by fluorescence of GFP or with an anti-JEAP antibody under a fluorescence microscope. JEAP-2-expressing cells were also confirmed similarity.

Figure 3:
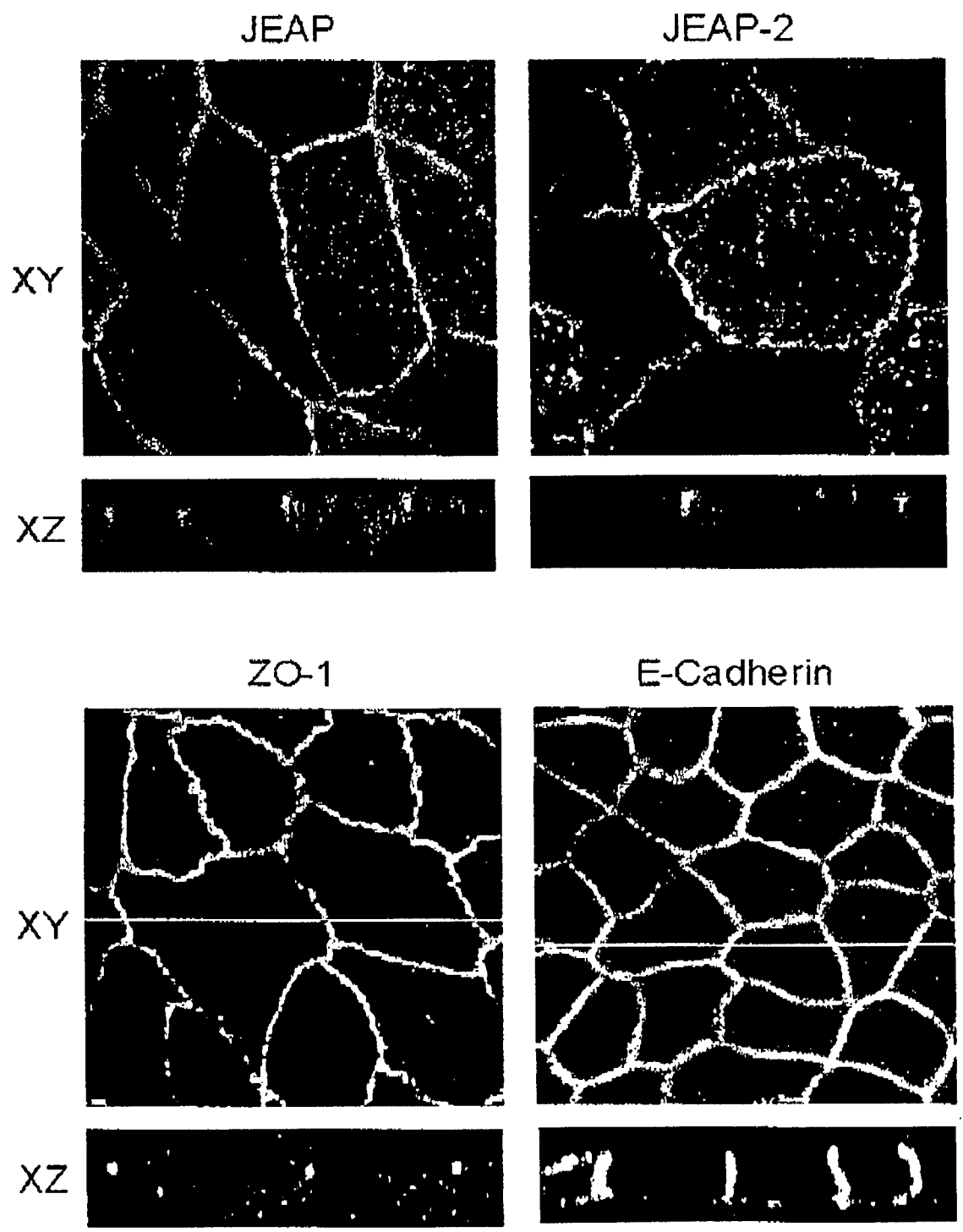
FIG. 3 is a stained image of MDCK cell (photograph) showing distributions of JEAP, JEAP-2, ZO-1 and E-cadherin.

Then, intracellular distribution of these proteins was examined by confocal microscopy comparing with those of ZO-1 and E-cadherin. As shown in FIG. 3, both of the transfected JEAP and JEAP-2 were accurately co-localized with ZO-1 at TJs. Computerized sectional images clearly indicated co-localization of JEAP and JEAP-2 which were densely accumulated, with ZO-1 at the apical region of the membrane of the gene-transfected MDCK cells. However, E-cadherin would appear to be localized at lower sites, which indicates that its distribution does not overlap the distribution of JEAP or JEAP-2. These findings indicate that both JEAP and JEAP-2 are concentrated at TJs.

Example 5

Expression of Mouse JEAP and JEAP-2 in Tissues in an Organism

Next, expression of JEAP and JEAP-2 in various tissues was examined.

Figure 4:
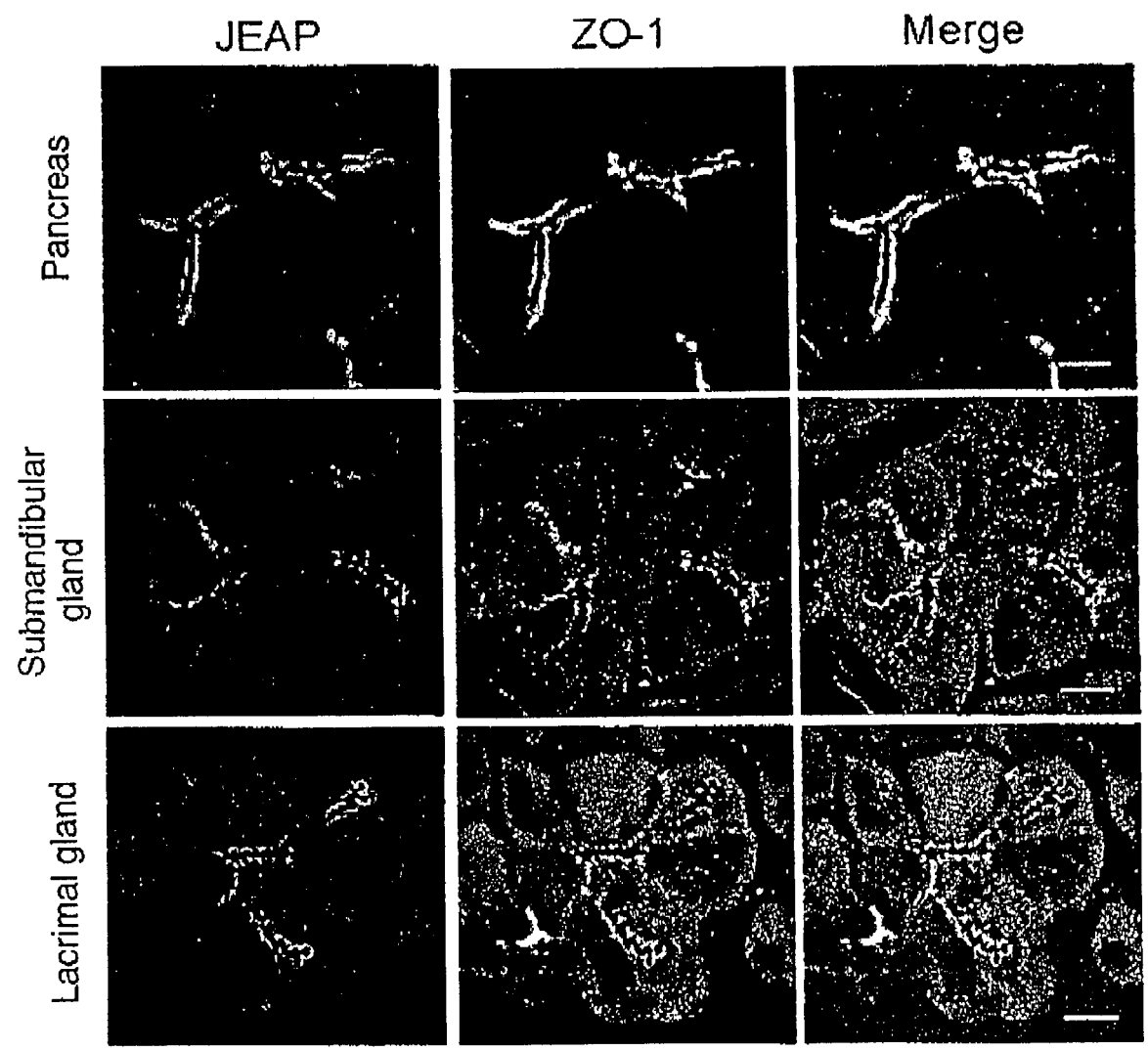
FIG. 4 is a stained image of tissue (photograph) showing distributions of JEAP and ZO-1 and an immuno-electron micrograph (photograph) showing distribution of JEAP in intercellular space of an exocrine gland.
Figure 4:
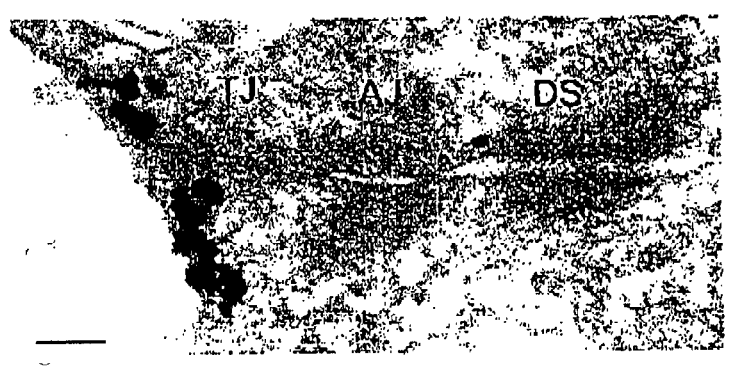

First, tissue distribution of JEAP was examined by detecting expression of JEAP in various mouse tissues (liver, brain, lung, kidney, spleen, testis, ovary, and heart) by Western blotting, and no JEAP was detected in any of these tissues. Then, the tissue distribution of JEAP was examined by immunohistochemical staining. JEAP was detected specifically in exocrine glands including pancreas, submandibular gland, lacrymal gland (FIG. 4), parotid gland, and sublingual gland, but not in brain, heart, liver, kidney, spleen, gallbladder, or small intestine. In exocrine glands, JEAP was expressed around the terminal portion of serous glands. In the terminal gland portion, JEAP showed a similar staining pattern to that of ZO-1. Observation by immuno-electron microscopy revealed that JEAP indeed localized at TJs but not at AJs or desmosomes, in the lacrymal gland (FIG. 4).

Figure 5:
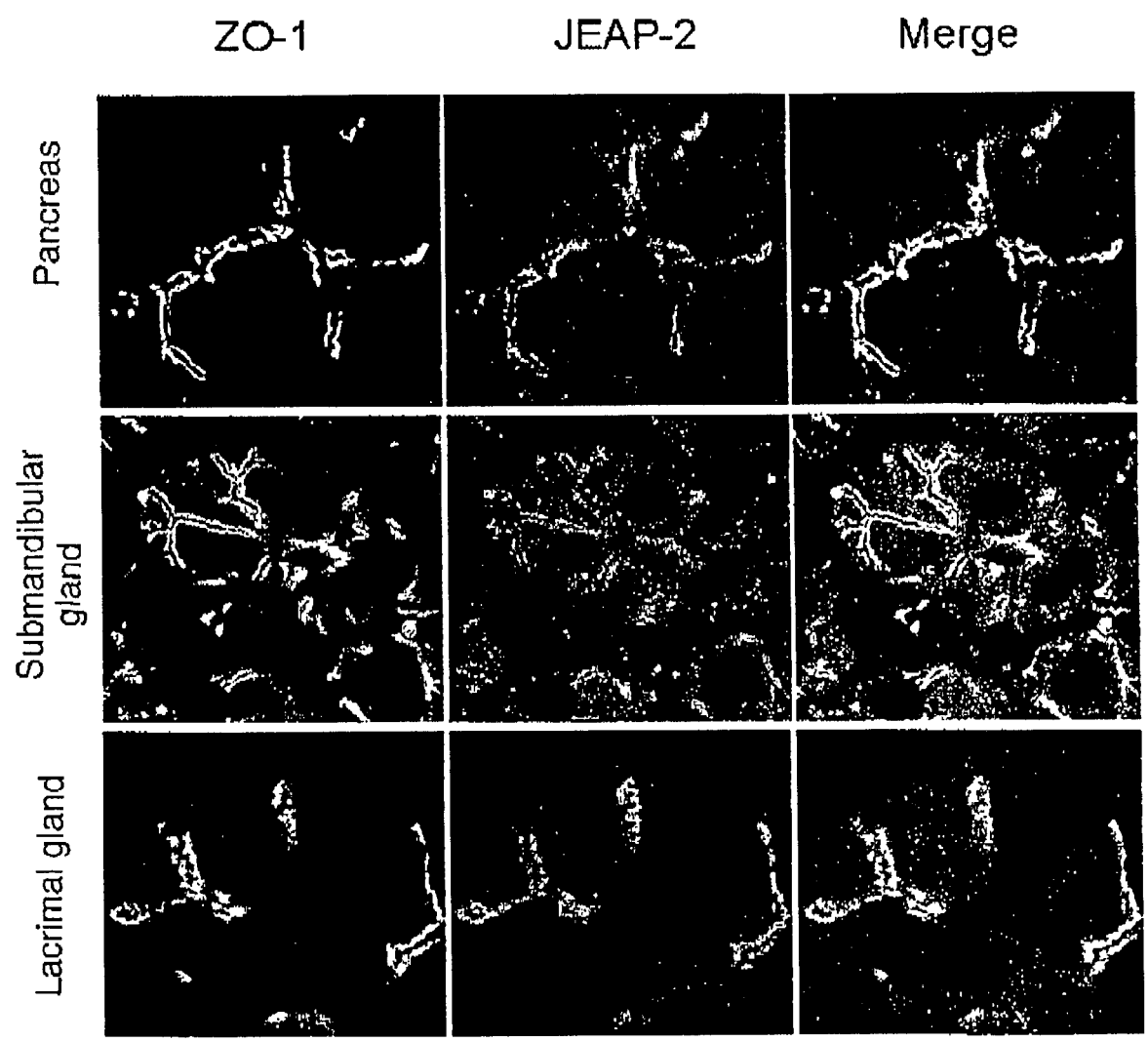
FIG. 5 is a stained image of tissue (photograph) showing distributions of JEAP-2 and ZO-1.
Figure 6:
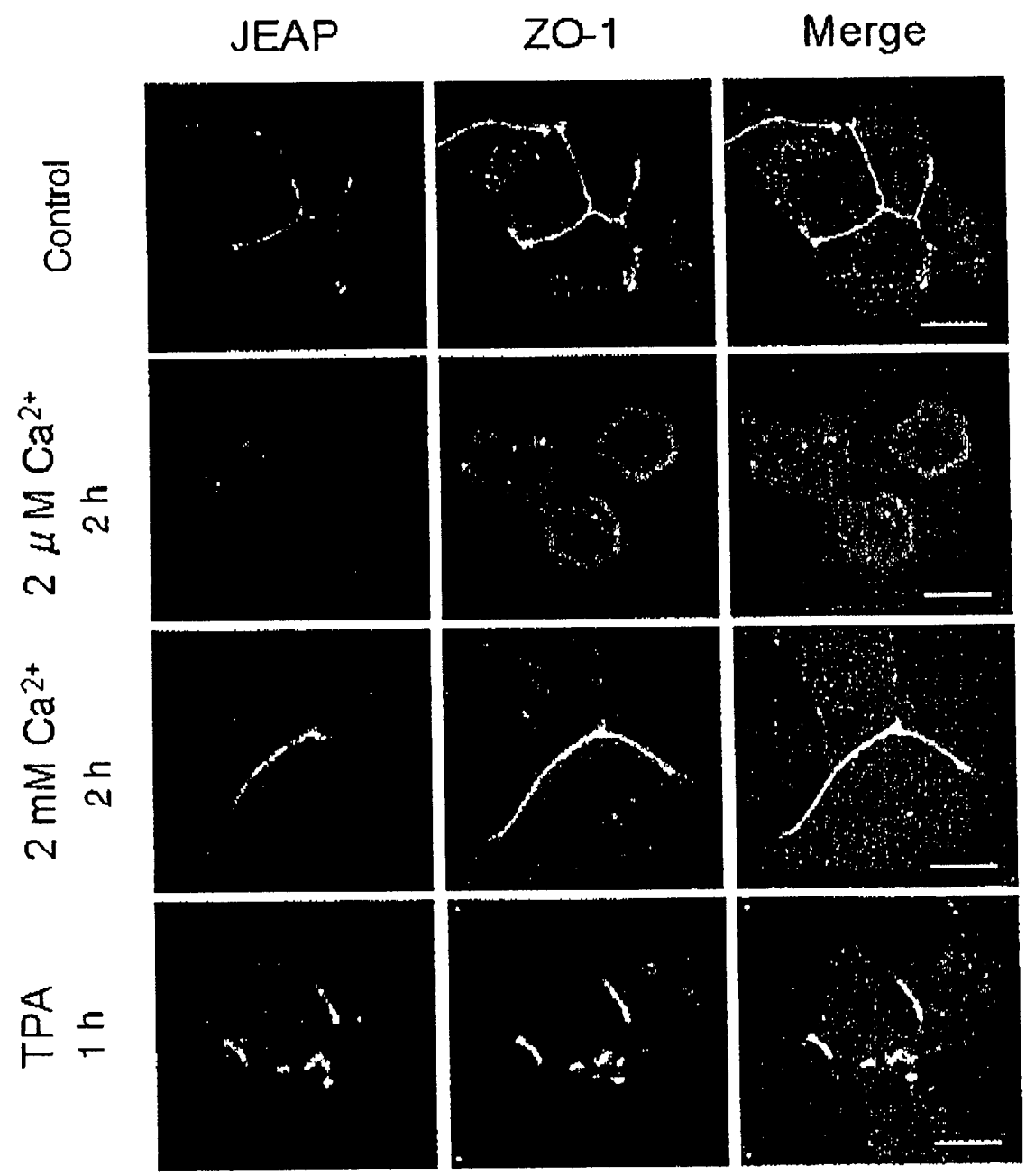
FIG. 6 is a stained image of MDCK cell (photograph) showing distributions of JEAP and ZO-1.

Then, the tissue distribution of JEAP-2 was examined by immunohistochemical staining. For JEAP-2 too, expression in exocrine glands such as pancreas, submandibular gland, and lacrymal gland (FIG. 5) was confirmed, but not in small intestine.

These findings indicate that JEAP and JEAP-2 have tissue specificity and localize particularly at TJs of exocrine glands in large amounts.

Example 6

Incorporation of JEAP into Cell-Cell Junctions Along with Other Components of TJs Finally, the behaviors of JEAP and other AJs and TJs components during the disruption and reformation of cell-cell junctions were monitored. For this purpose, MDCK/EcoVR cells stably expressing JEAP as prepared in Example 4 were used to perform the experiment. It has been known that when MDCK cells are cultured in the presence of 2 μM $Ca^{2+}$ for 2 hours, AJs and TJs are disrupted and the staining of the AJ and TJ components except ZO-1 disappear from the periphery of the plasma membrane. Further, it has also been known that when the cells in this state are recultured in the presence of 2 mM $Ca^{2+}$ for 2 hours, AJs and TJs relocalize where all the AJ and TJ components reconcentrate at the cell-cell junctions.

In culturing in an ordinary medium, JEAP co-localized at the cell-cell junctions together with ZO-1 in the same manner as shown in Example 4. When the cells were cultured in the presence of 2 μM $Ca^{2+}$ for 2 hours, the immunofluorescence signal for JEAP disappeared, whereas the fluorescence signal for ZO-1 partially remained near the plasma membrane though the intensity decreased. When the cells in this state were cultured in the presence of 2 mM $Ca^{2+}$ for 2 hours, JEAP reconcentrate at the cell-cell junctions together with ZO-1. Furthermore, it has been known that culturing at 2 μM Ca²⁺ for 2 hours followed by further culturing for 1 hour with addition of 100 nM 12-O-tetradecanolylphorbol 13-acetate (TPA) results in reformation of a structure similar to that of TJs but does not result in reformation of AJs. It has been shown that TJ components, i.e., claudin, occludin, JAM, nectin, ZO-1 and afadin concentrate at the structural site similar to TJs of cell-cell junctions induced with TPA but AJ components, i.e., E-cadherin, α-catenin and β-catenin, do not concentrate there. Here, JEAP along with ZO-1 concentrated at the structural site similar to TJs of cell-cell junctions induced with TPA. In the same manner, JEAP concentrated at the structural site similar to TJs of cell-cell junction induced with TPA along with claudin-1 and accludin.

These findings indicate that JEAP is incorporated into TJs along with other components of TJs.

---

What is claimed is:

1. An isolated DNA encoding a protein of the following (a) or (b):
   (a) a protein having an amino acid sequence shown in SEQ ID NO:4; and
   (b) a protein having an amino acid sequence having deletion, substitution or addition of a single amino acid in an amino acid sequence shown in SEQ ID NO:2 or SEQ ID NO:4, and localizing at tight junctions, with a proviso that the protein is not a protein having an amino acid sequence shown in SEQ ID NO:2.

2. An isolated DNA according to claim 1, having a nucleotide sequence shown in SEQ ID NO:3.

3. A recombinant vector comprising the DNA as defined in claim 1.

4. A transformant obtained by transforming a host with the DNA as defined in a claim 1.

5. A method for producing a protein localizing at tight junctions, comprising:
culturing the transformant as defined in claim 4; and
collecting a protein localizing at tight junctions expressed by the transformant from the culture.

6. A recombinant vector comprising the DNA as defined in claim 2.

7. A transformant obtained by transforming a host with the DNA as defined in claim 2.

8. A method for producing a protein localizing at tight junctions, comprising:
culturing the transformant as defined in claim 7; and
collecting a protein localizing at tight junctions expressed by the transformant from the culture.

* * * * *